US009778176B2

(12) United States Patent
Sorvajärvi et al.

(10) Patent No.: US 9,778,176 B2
(45) Date of Patent: Oct. 3, 2017

(54) MEASUREMENT OF GASEOUS COMPOUND USING SPECTROSCOPY

(75) Inventors: Tapio Sorvajärvi, Lempäälä (FI); Juha Toivonen, Tampere (FI); Juha Roppo, Lempäälä (FI); Jaani Silvennoinen, Tampere (FI); Sonja Enestam, Turku (FI)

(73) Assignee: VALMET TECHNOLOGIES OY, Espoo (FI)

( * ) Notice: Subject to any disclaimer, the term of this patent is extended or adjusted under 35 U.S.C. 154(b) by 364 days.

(21) Appl. No.: 14/406,431

(22) PCT Filed: Jun. 8, 2012

(86) PCT No.: PCT/FI2012/050579
§ 371 (c)(1),
(2), (4) Date: Jan. 20, 2015

(87) PCT Pub. No.: WO2013/182735
PCT Pub. Date: Dec. 12, 2013

(65) Prior Publication Data
US 2015/0138544 A1 May 21, 2015

(51) Int. Cl.
*G01N 21/39* (2006.01)
*G01N 21/63* (2006.01)
*G01N 33/00* (2006.01)

(52) U.S. Cl.
CPC ........... *G01N 21/39* (2013.01); *G01N 21/631* (2013.01); *G01N 33/0062* (2013.01); *G01N 2201/06113* (2013.01)

(58) Field of Classification Search
USPC .......................................................... 356/437
See application file for complete search history.

(56) References Cited

U.S. PATENT DOCUMENTS 4,341,470 A * 7/1982 Parker ................ G01N 21/3103 356/307
5,153,673 A 10/1992 Amirav
2008/0165363 A1 7/2008 Gusev

FOREIGN PATENT DOCUMENTS

JP 2006300760 A 11/2006
JP 2009276308 A 11/2009
(Continued)

OTHER PUBLICATIONS

Hess et al., "Application of an InGaAsP Diode Laser to Probe Photodissociation Dynamics: I Quantum Yields From n- and i-C3F7I and CH3I by Laser Gain vs Absorption Spectroscopy," J. Chem Phys., vol. 84(4), pp. 2143-2149, Feb. 15, 1986.
(Continued)

*Primary Examiner* — Kara E Geisel
*Assistant Examiner* — Amanda Merlino
(74) *Attorney, Agent, or Firm* — Oliff PLC

(57) ABSTRACT

The method includes guiding a light beam to a first optical path, the light beam being attenuated to an attenuated light beam and detecting a first value indicative of a first intensity of the attenuated light beam. The method further includes generating a last light pulse, dissociating at least part of the gas compound molecules (optionally excited) or dissociated parts thereof (optionally excited) on the first optical path to first part atoms, molecules, ions, or radicals, and to another part using the last light pulse, the light beam being further attenuated by absorption to the first part atoms, molecules, ions, or radicals on the first optical path. The method further includes detecting a second value indicative of a second intensity of the attenuated light beam and determining, using the first and second values, the gas compound content of the gas mixture. A gas compound measuring device measures uses the method.

15 Claims, 11 Drawing Sheets

510
710b
Cl
Pb
Cl
516
hc/$\lambda_{p2}$
512
Cl 525
PbCl 530
515
hc/$\lambda_{p1}$
710a
531
170 $\lambda_b$
Pb
520
175
$\lambda_b$
Cl
532

(56) References Cited

FOREIGN PATENT DOCUMENTS

| | | | |
|---|---|---|---|
| WO | 01/27593 | A1 | 4/2001 |
| WO | 2013/083871 | A1 | 6/2013 |

OTHER PUBLICATIONS

Lintz and Bouchiat, "Dimer Destruction in a Cs Vapor by a Laser Close to Atomic Resonance," Physical Review Letters, vol. 80 (12), pp. 2570-2573, Mar. 23, 1998.
Monkhouse, "On-line Spectroscopic and Spectrometric Methods for the Determination of Metal Species in Industrial Processes," Progress in Energy and Combustion Science, vol. 37, pp. 125-171, 2011.
Ravishankara et al., "Pulsed Laser Photolysis-long Path Laser Absorption Kinetics Study of the Reaction of Methylperoxy Radicals and NO2," J. Chem. Phys., vol. 73(8), pp. 3743-3749, Oct. 15, 1980.
Schlosser et al., " Diode Laser Based in situ Detection of Alkali Atoms: Development of a New Method for Determination of Residence-time Distribution in Combustion Plants," Applied Physics B, vol. 75, pp. 237-247, 2002.
Wolfrum, "Laser Induced Chemical Reactions in Combustion and Industrial Processes," Laser Chem., vol. 6, pp. 125-147, 1986.
Sorvajärvi et al., "Optical Detection of Potassium Chloride Vapor Using Collinear Photofragmentation and Atomic Absorption Spectroscopy," Optics Letters, vol. 37(19), pp. 4011-4013, Oct. 1, 2012.
Greger et al., "In Situ Alkali Concentration Measurements in a Pressurized, Fluidized-Bed Coal Combustor by Excimer Laser Induced Fragmentation Fluorescence," Twenty-Sixth Symposium (International) on Combustion/The Combustion Institute, pp. 3301-3307, 1996.
Dec. 13, 2012 International Search Report issued in International Application No. PCT/FI2012/050579.
Oct. 9, 2012 Office Action and Search Report issued in Finnish Patent Application No. 20116232.
Sep. 23, 2014 International Preliminary Report on Patentability issued in International Application No. PCT/FI2012/050579.
Jun. 19, 2014 Written Opinion of the International Preliminary Examining Autority issued in International Application No. PCT/FI2012/050579.
Dec. 13, 2012 Written Opinion of the International Searching Authority issued in International Application No. PCT/FI2012/050579.

* cited by examiner

MEASUREMENT OF GASEOUS COMPOUND USING SPECTROSCOPY

FIELD OF THE INVENTION

The invention relates to a method for measuring the content of a gaseous compound from a gas mixture using optical spectroscopy. The invention relates to a method, wherein in the gas mixture and the gaseous compound are results of a thermal process. The thermal process may be e.g. one of combustion, pyrolysis, torrefaction, and gasifying. The invention further relates to a device arranged to measure the content of the gaseous compound from the gas mixture using optical spectroscopy, wherein the gaseous compound may be a result of a thermal process.

BACKGROUND OF THE INVENTION

Environmental aspects and the increasing price of the fossil fuels has increased the interest in renewable fuels in power production. One alternative, as a largely $CO_2$ neutral fuel, is biomass. Biomass may be e.g. harvested as residues from forest industry. In addition, the biomass may comprise at least one of agricultural waste, peat, stubs, stumps, branches, and waste wood such as bark, wooden construction debris, and wood product residuals. Biomass may be used in a thermal process. E.g. biomass may be burned to produce energy. Alternatively, biomass may be gasified to produces synthesis gases, which may be further processed to biofuel. Still further, biomass may be treated in a pyrolysis process to produce pyrolysis gas, which may be condensed to pyrolysis oil. Still further, biomass may be treated in a torrefaction process to produce biocoke, which may be utilized elsewhere in combustion and/or gasification processes. These thermal processes produce a mixture of various gases, e.g. flue gas, synthesis gas, pyrolysis gas, or torrefaction gas. The content of a specific gaseous compound in the gases is often of interest because of various reasons. E.g. flue gases, as the results of combustion of biomass, cause corrosion and slagging problems in combustion boilers. One cause of the problems is alkali hydroxide vapors, which are formed during combustion. In order to quantify the corrosion problem, the hydroxide content of the flue gases needs to be measured. In addition to hydroxides, metal chlorides such as $PbCl_2$, metal carbonates such as $K_2CO_3$, and metal sulfates such as $K_2SO_4$ may cause similar problems.

In general, optical spectroscopy may be utilized to measure the content of harmful gases from the gases. Methods include absorption spectroscopy, wherein the attenuation of light is measured. As different gaseous compounds absorb light differently, the attenuation spectrum may be used to deduce the content of different gaseous compounds. The sensitivity of the method is relatively low, being in the ppm (parts per million, $10^{-6}$) range. This is partly due to low absorption of the gases and partly due to fluctuations in the flue gas.

Optical methods include also those based on Excimer Laser Induced Fluorescence. In these methods, the alkali chloride molecules are dissociated, and the released alkali atom is excited using an excimer laser. As the alkali atom relaxes from the excited state, a photon is emitted. The wavelength of the photon corresponds to the alkali species and the alkali content is measured from the emission spectrum. In principle, the sensitivity of the method is in the ppb (parts per billion, $10^{-9}$) range. However, in a combustion environment, scattering of light e.g. from soot particles, dilutes the sensitivity of the methods.

SUMMARY OF THE INVENTION

A method for measuring the content of a gas compound in a gas mixture is presented. The method is especially useful in cases, where the gas mixture is a product gas of a thermal process. By the method, a sensitivity in the ppb ($10^{-9}$) range can be achieved.

An embodiment of the method comprises generating a light beam, wherein the light beam comprises photons having a beam wavelength, guiding the light beam to a first optical path, wherein the first optical path runs through a space containing the gas mixture comprising the gas compound, whereby the light beam is attenuated to an attenuated light beam and detecting a first value indicative of a first intensity of the attenuated light beam.

The embodiment further comprises generating a last light pulse, wherein the last light pulse comprises photons having a first pulse wavelength, optionally generating another light pulse, dissociating at least part of the gas compound molecules or at least part of excited gas compound molecules on the first optical path to at least two dissociated parts using the last light pulse or the another light pulse, dissociating at least part of the gas compound molecules, at least part of excited gas compound molecules, at least part of the dissociated parts, or at least part of the excited dissociated parts on the first optical path to first part atoms, molecules, ions, or radicals, and to another part using the last light pulse, whereby the light beam is further attenuated to an attenuated light beam by absorption to the first part atoms, molecules, ions, or radicals on the first optical path, detecting a second value indicative of a second intensity of the attenuated light beam, and determining, using the first value and the second value, the gas compound content of the gas mixture.

In an embodiment the method, the gas compound consists of gas compound molecules, and the gas compound molecule is not an alkalihalide molecule, wherein the alkalihalide molecule has form $MH^a$, wherein M is an alkali metal atom from the group of Li, Na, K, Ru, Cs, and Fr, and $H^a$ is a halogen atom from the group of F, Cl, Br, I, and At.

Further embodiments of the method are disclosed in the examples 2-27.

For the application of the method, a device for measuring the content of a gaseous compound in a gas mixture is disclosed.

An embodiment of the device comprises a light beam source, arranged to emit a light beam comprising photons having a beam wavelength and a photodetector, wherein a first optical path is arranged optically between the photodetector and the light beam source, a space, through which the first optical path is arranged to run, is arranged to contain the gas mixture absorbing the light beam, the light beam is arranged to be attenuated to an attenuated light beam by said absorption of the light beam, and the photodetector is arranged to detect a first value indicative of a first intensity of the attenuated light beam.

The embodiment further comprises at least a first light pulse source, wherein the first light pulse source is arranged to generate a last light pulse comprising photons having a first pulse wavelength, at least part of the photons dissociating at least part of gas compound molecules or dissociated parts on the first optical path to first part atoms, molecules, ions, or radicals, and to another part, wherein the light beam is further attenuated to the attenuated light beam by absorption to first part atoms, molecules, ions, or radicals on the first optical path, wherein the dissociated parts have optionally been produced from the gas compound molecules by dissociation using another light pulse, the photodetector is arranged to detect a second value indicative of a second intensity of the attenuated light beam, and the device comprises a data processing unit arranged to determine, using the first value and the second value, the gas compound content in the gas mixture.

Other features of embodiments of the device are disclosed in the examples 29 to 49.

The device may be comprised by a boiler, as disclosed in the example 50. The device may be comprised by a gasification reactor, as disclosed in the example 51. The device may be comprised by a pyrolysis reactor, as disclosed in the example 52. The device may be comprised by a torrefaction reactor, as disclosed in the example 53.

DETAILED DESCRIPTION OF THE INVENTION

A method and a device for measuring the content of a gas compound in a gas mixture is presented. The term gas mixture refers to a mixture comprising at least one gas compound. Typically a gas mixture comprises several gas compounds. In addition, the gas mixture may comprise solid and liquid compounds, such as particles or droplets. The term gas compound refers to a substance that is in its gaseous form in the measurement temperature and pressure.

The gas mixture may be e.g. a result of a thermal process. The thermal process may be e.g. one of combustion, pyrolysis, torrefaction, and gasifying. In particular, the temperature of the gas mixture may be relatively high, e.g. from 300° C. to 1300° C. However, the method is applicable also in room temperature, and below. E.g. the gas mixture may have a temperature greater than −50° C. The at least one gas compound of the gas mixture is in its gaseous state in the temperature and the pressure. Other compounds may be is liquid or solid state, as discussed above. The content of the gas compound of the gas mixture may be measured with the method that will be disclosed, e.g. by using a device that will be disclosed.

Measurement is based on absorption spectroscopy. In the method, a light beam is generated, the light beam is guided through the gas mixture to be measured, along an optical path, whereby a part of the light is absorbed and scattered by the gas mixture, and the intensity of the light beam having passed through the gas mixture is measured. Other steps of the method will be described in more detail later. Referring to FIGS. 1*a*-1*d*, the gas mixture may be located in a space 110. The space 110 may be limited by the walls 102 (e.g. walls 102*a*1, 102*a*2, 102*b*1, 102*b*2, 102*c*, 102*d*1, 102*d*2). The space 110 is not necessarily limited by any walls. In this case, the content of the gas compound from ambient may be measured. Moreover, the device may be installed to the ambient and can be used as such. However, often the gas mixture is located in a channel or a vessel limited by at least one wall (e.g. a tube).

Figure 1A:
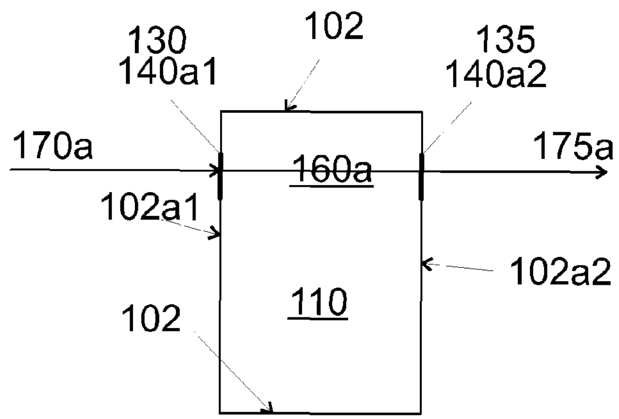
FIGS. 1*a*-1*d* show some optical paths between an optical inlet and an optical outlet of a gas mixture container.

The term "wall" is used only to describe an element separating the space 110 from the exterior. At least one wall 102 comprises at least one optical inlet 130, such as a window 140 or a hole 132, for optical measurements. In FIG. 1*a*, a window 140 is transparent so that light can propagate through the window. Preferably the light of the measuring light beam 170 (170*a*, 170*b*, 170*c*) is not significantly attenuated while travelling through the window. The wavelength of the light beam 170 will be defined in more detail later. A wall 102 may comprise at least one optical outlet 135, such as a window 140 or a hole 132. In FIG. 1*a*, the window 140*a*1 is also marked with the reference number 130 for optical inlet. In FIG. 1*a*, the window 140*a*2 is also marked with the reference number 135 for optical outlet. In case a hole 132 (FIG. 1*d*; 132*d*1, 132*d*2) is used as an optical inlet, air or other gas may be blown through the hole 132 into the space 110 in order to retain the gas mixture in the space 110. In the method or with the device, a light beam 170 (170*a*, 170*b*, 170*c*, 170*d*) is generated and guided through the optical inlet to the space 110. An optical path may also be generated without any wall, in which case an optical inlet or an optical outlet is not needed.

Figure 1B:
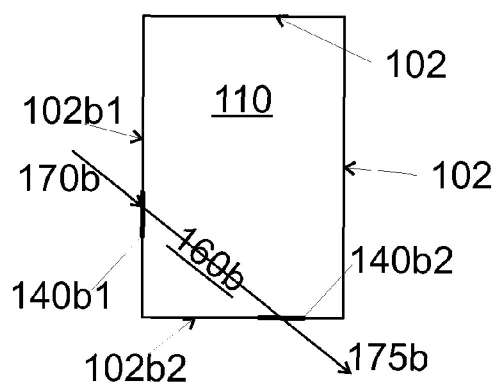
Figure 1C:
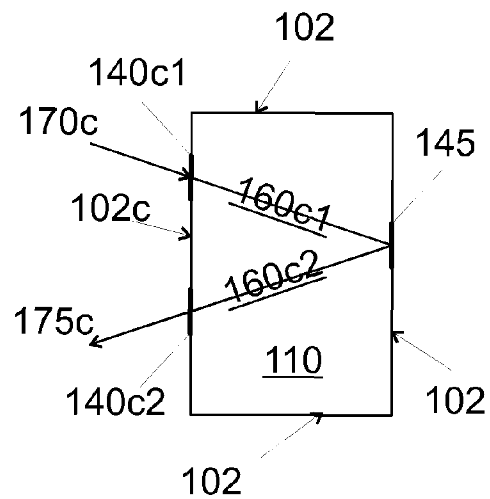
Figure 1D:
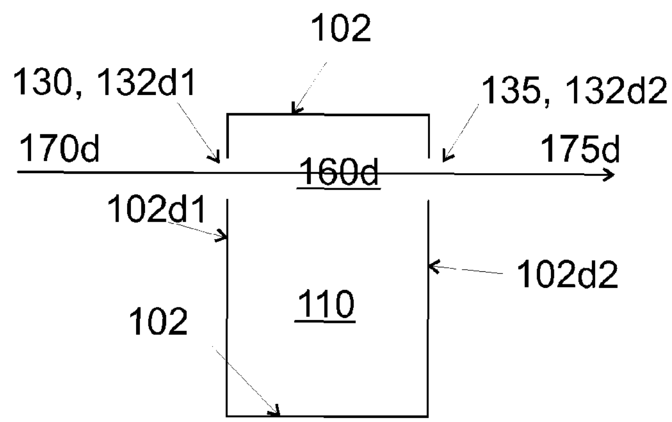

Referring to FIGS. 1*a*-1*d*, in between an optical inlet 130 and an optical outlet 135, in the space 110, a first optical path 160 is formed. When the light beam 170 enters the optical inlet 130, the light beam travels through the first optical path 160 to the optical outlet 135. The content of the gas compound in the gas mixture, in the space 110, at the first optical path 160, will be measured as discussed later. In FIGS. 1*a*-1*c* a window 140*a*1, 140*b*1 or 140*c*1 serves as the optical inlet 130 and another window 140*a*2, 140*b*2, 140*c*2 serves as the optical outlet 135. In FIG. 1*d*, the hole 132*d*1 serves as the optical inlet 130, and the hole 132*d*2 serves as the optical inlet 135.

A preferred embodiment for the first optical path 160*a* is shown in FIG. 1*a*, wherein a first wall 102*a*1 comprises a first window 140*a*1, a second wall 102*a*2 comprises a second window 140*a*2, the first wall 102*a*1 is essentially parallel to the second wall 102*a*2, and the optical path 160*a* is essentially perpendicular to the first window 140*a*1 and the second window 140*a*2. The windows may be essentially parallel to the wall. The wall 102 may be curved. In a preferred embodiment, the windows 140*a*1 and 140*a*2 are essentially planar. A light beam 170*a* enters and penetrates the first window 140*a*1, travels along the first optical path 160*a* to the second window 140*a*2, enters and penetrates the second window 140*a*2, and exits the second window as an attenuated light beam 175*a*. The first optical path 160*a* extends through the space 110.

Other embodiments are shown in FIGS. 1*b* and 1*c*. In FIG. 1*b*, a light beam 170*b* enters and penetrates the first window 140*b*1, travels along a first optical path 160*b* to the second window 140*b*2, enters and penetrates the second window 140*b*2, and exits the second window as the attenuated light beam 175*b*. The first window 140*b*1 is arranged in an angle with respect to the second window 140*b*2. In the FIG. 1*b*, the angle is essentially a right angle. However, also other angles are possible.

In FIG. 1*c*, a light beam 170*c* enters and penetrates the first window 140*c*1, travels along a first part 160*c*1 of the first optical path to a reflector 145. A part of the wall 102 may act as the reflector 145. The reflector may reflect or scatter the light beam such that at least part of the light beam is guided to a second part 160*c*2 of the optical path. The reflected or scattered part of the light beam travels along a second part 160*c*2 of the first optical path to the second window 140*c*2, enters and penetrates the second window 140*c*2, and exits the second window as the attenuated light beam 175*c*. The first optical path comprises its parts 160*c*1 and 160*c*2. The first window 140*c*1 is arranged to a wall 102*c*, and the second window 140*b*2 is arranged to the same wall 102*c*. If a reflector 145 is used, a window 140 may operate both as the first window and as the second window, i.e. as both the optical inlet 130 and the optical outlet 135 (not shown).

In FIG. 1*d*, a light beam 170*d* penetrates a first hole 132*d*1 (the optical inlet 130), travels along the first optical path 160*d* to a second hole 132*d*2 (the optical outlet 135), and exits the second hole 132*d*2 as the attenuated light beam 175*d*. A hole 132 may be used instead of a window also in the embodiments of FIGS. 1*b* and 1*c*. Moreover, one hole 132 may serve both as the optical inlet 130 and as the optical outlet 135. The walls 102 in FIG. 1*d* are arranged as discussed in the context of FIG. 1*a*.

In FIGS. 1*a*-1*d*, the first optical path 160 is located optically between the optical inlet 130 and the optical outlet 135. In case a reflector 145 is used, the optical path is not necessarily physically between the optical inlet and the optical outlet, as illustrated in FIG. 1*c*. The wording "optically between" means that light entering the optical inlet may travel along the first optical path to the optical outlet (or the optical inlet, if a hole or a window acts both as the optical inlet and as the optical outlet).

Measurement Principle, Single-Step Dissociation

Having described preferable environments for the measurement configuration, the measurement principle will be described in more detail. To overcome the problems indicated in the background, the sensitivity of the measurements is increased in two ways:

(1) by increasing absorption of the gas mixture corresponding to the wavelength(s) of the light beam 170, and (2) by shortening the measurement time in order to obtain temporarily stationary measurement conditions.

The measurement is based on absorption spectroscopy. The method comprises:

generating a light beam 170, wherein the light beam 170 comprises photons having a beam wavelength $\lambda_b$, guiding the light beam 170 to a first optical path 160, wherein the first optical path 160 runs through a space 110 containing the gas mixture, whereby the light beam 170 is attenuated to an attenuated light beam 175, and detecting a first value indicative of a first intensity $I_{k0}$ of the attenuated light beam 175.

In the method, the sensitivity is improved by increasing the absorption of the gas mixture for the beam wavelength $\lambda_b$. It is noted, however, that in general, the light beam 170 comprises photons having the wavelength $\lambda_b$, and may further comprise photons having a different wavelength. In a preferred embodiment, a monochromatic light beam source (a laser) is used to generate the light beam 170.

The absorption is increased by dissociating the molecules of the gas compound on the first optical path 160 to two parts: a first part and a second part. The first part may be an atom, a molecule, and ion, or a radical. The term radical refers to an atom, a molecule, or an ion with unpaired electrons or an open shell configuration. These unpaired electrons may cause radicals to be highly chemically reactive. The second part may be an atom, a molecule, an ion, or a radical. At least one of the first part and the second part may be in an excited state or in a relaxed state.

Figure 2A:
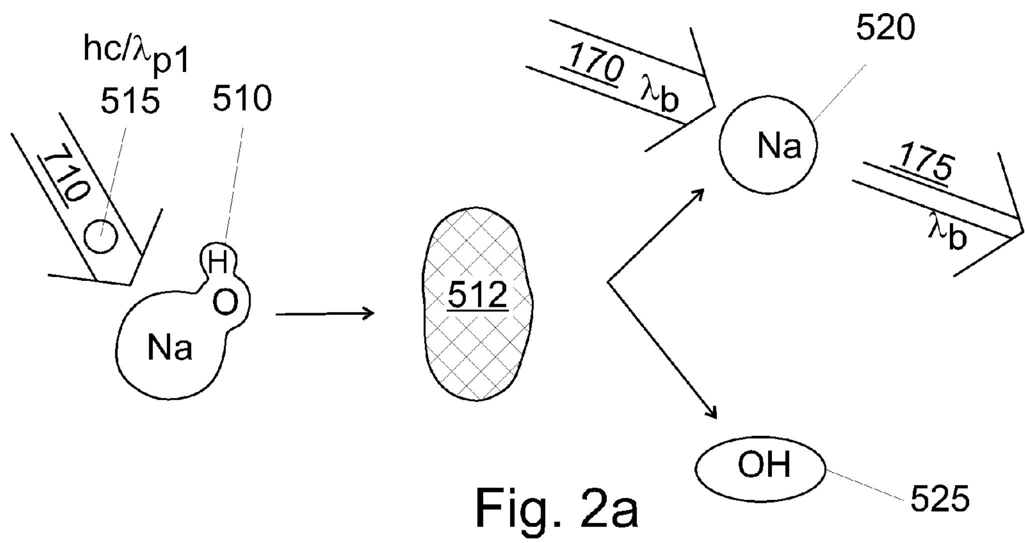
FIG. 2*a* shows the dissociation of a sodium hydroxide molecule to a sodium atom and a hydroxide molecule using one photon of an optical pulse.

The dissociation process is schematically shown in FIG. 2*a* for sodium hydroxide. In the method, the molecule is dissociated to two parts using a light pulse 710. In FIG. 2*a*, the sodium hydroxide molecule is first excited to a molecule 512 in a dissociative state by using a light pulse 710. The light pulse 710 comprises photons 515 having a wavelength $\lambda_{p1}$. This photon 515 also has the energy $hc/\lambda_{p1}$. The energy is generally relatively high, e.g. the wavelength $\lambda_{p1}$ is short. High energy is needed to excite the molecule 510 to the molecule 512 in the dissociative state. The light pulse 710 need not to be monochromatic. Preferably the light pulse 710 is monochromatic or essentially monochromatic and has a first pulse wavelength $\lambda_{p1}$.

Figure 2B:
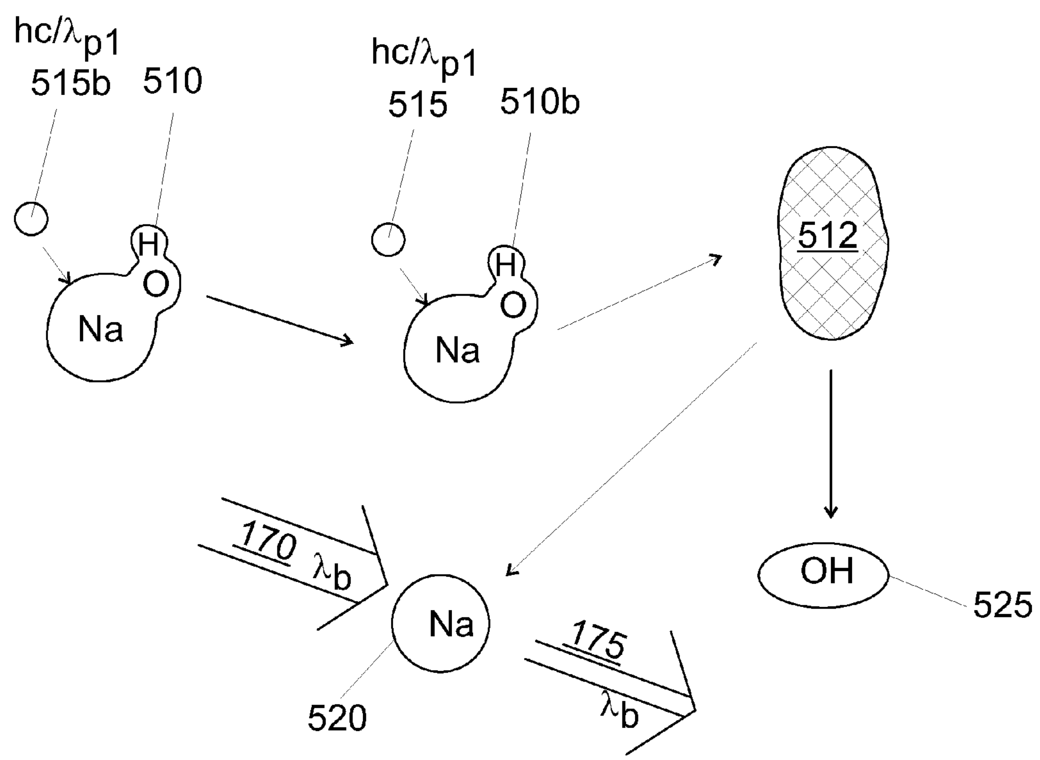
FIG. 2*b* shows the dissociation of a sodium hydroxide molecule to a sodium atom and a hydroxide molecule using two photons of an optical pulse.

Referring to FIG. 2*b*, the molecule may alternatively be dissociated to at least two parts using two photon excitation or multiple photon excitation. In FIG. 2*b*, the molecule 510 is dissociated to two parts using a light pulse 710 such that the molecule is excited to the dissociative state with at least two photons of the pulse or with at least two photons of at least two pulses. In FIG. 2*b*, the sodium hydroxide molecule 510 is first excited to an excited state 510*b*, such as an energy state or a virtual state, with a photon 515*b* of an optical pulse, such as the optical pulse 710. Thereafter, the excited sodium hydroxide molecule 510*b* is further excited to a dissociative state 512 with another photon 515 of the optical pulse 710. This excitation may be referred to as "two photon excitation". As for sake of clarity, the pulse that comprises the photons 515 that excite the excited gas molecule 510*b* to the dissociative state 512 may be referred to as the last light pulse.

Even if not shown in the FIGS. 2*a* and 2*b*, a gas compound molecule 510 comprising three atoms may be excited with at least one photon (515, 515*b*) to an excited state 512 such that it dissociates to three parts. For example $PbBr_2$ can be excited, e.g. with one photon, to the dissociative state 512 such that the dissociative state dissociates to Pb, Br, and Br.

In the dissociative state, the molecule 512 is unstable, meaning that the molecule dissociates to the first part 520 and the second part 525. Referring to FIG. 2*a*, the first part 520 may refer to sodium atom. Referring to FIG. 2*a*, the second part 525 may refer to hydroxide molecule.

Figure 3A:
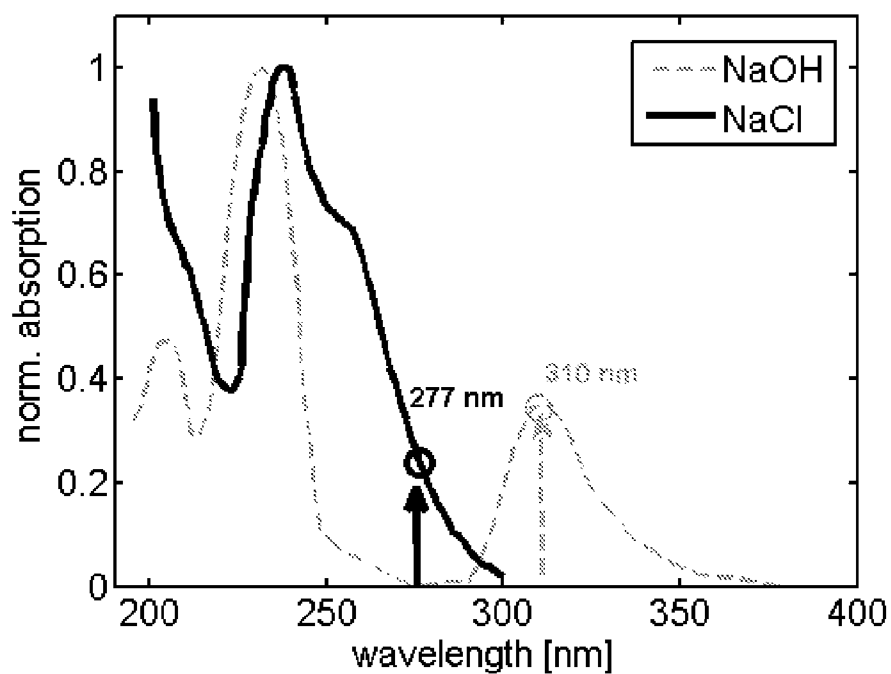
FIG. 3*a* shows the normalized absorption of sodium hydroxide and sodium chloride molecules as function wavelength.

The pulse wavelength (or pulse wavelengths in case on two or multiple photon excitation with at least two pulses) is selected so as to dissociate the gas compound molecule 510. Referring to FIG. 3*a*, for example in the case a sodium hydroxide molecule 510 is to be dissociated, a light pulse comprising photons having a wavelength shorter than about 380 nm may be used. However, photons in the wavelength range from about 260 nm to about 290 nm do not significantly dissociate the NaOH molecules, as depicted in FIG. 3*a*. The wavelength of the pulse will be discussed in more detail later.

In the method and/or the device, the wavelength(s) of the light beam is selected such that the light beam 170 comprises photons having the wavelength $\lambda_b$. Moreover, the wavelength $\lambda_b$ is selected such that it corresponds to the absorption profile of the first part 520. The wavelength $\lambda_b$ corresponds to the absorption profile provided that the absorption cross section of the first part 520 (FIGS. 2*a* and 2*b*) and for the wavelength $\lambda_b$ is greater than 1/1000 (one thousandth) of the maximum absorption cross section for the first part 520. Preferably the first wavelength $\lambda_b$ corresponds to the wavelength of absorption maximum. Moreover, the light beam 170 used for measurements comprises photons having the beam wavelength, but may comprise photons having other wavelengths.

As the wavelength(s) of the light pulse and the light beam are such selected, after dissociation, the light beam 170 is attenuated to the attenuated light beam 175, among other things, due to the absorption to the first part 520, as depicted in FIGS. 2*a* and 2*b*. It is noted, however, that also the gas molecules 510 are located on an optical path such that also the gas molecules 510 are illuminated by the light beam 170. However, the gas molecules 510 do not significantly absorb the light beam 170; significantly meaning in comparison to the absorption to the first part 520 atoms molecules, ions, or radicals.

Figure 3B:
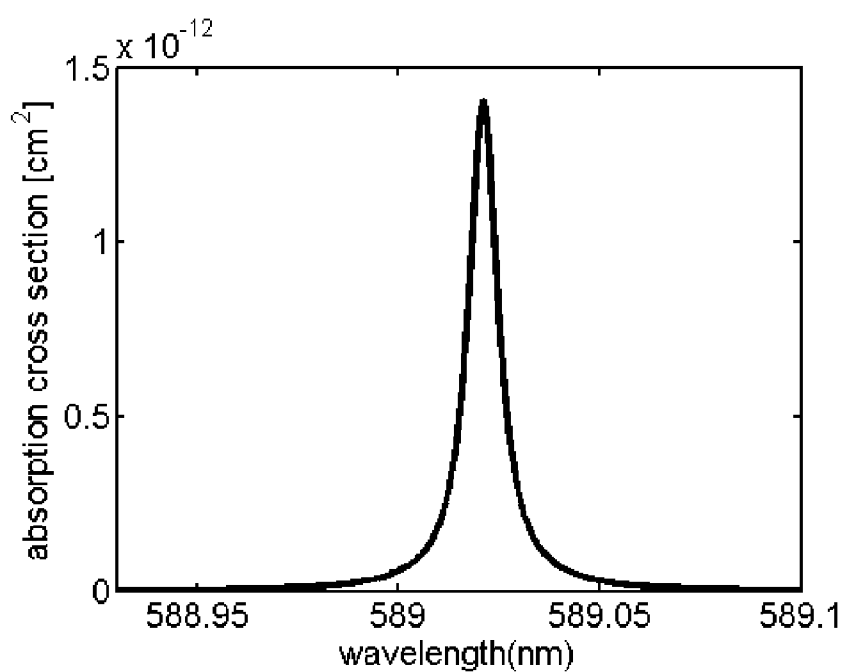
FIG. 3*b* shows the absorption cross section of sodium atom as function of wavelength.

Referring to FIG. 2*a*, the first part may be a sodium atom. FIG. 3*b* shows a calculated absorption cross section for a sodium atom that has been produced by dissociation of a NaOH molecule. The location, shape, and height of the peak depends on the first part to be measured. FIG. 3*b* serves as an example. As seen from FIG. 3*b*, for sodium the wavelength $\lambda_b$ may be used, wherein $\lambda_b$ may be selected from the range from 588.99 nm to 589.05 nm. Preferably the wavelength $\lambda_b$ is selected to be close to the wavelength corresponding the peak shown in FIG. 3*b*. Sodium is known to have also other absorption peaks.

Alternatively, any other wavelength corresponding to the absorption profile of sodium may be used as the first wavelength $\lambda_b$. For example, it is known that sodium has absorption peaks also near the wavelengths 589.6 nm, 330 nm, and 285 nm. Furthermore, an excited sodium atom has an absorption peak near the wavelength 818 nm. The selectivity of the sodium atom (i.e. the dissociated first part) is utilized in the embodiments of the invention. Since the absorption cross section has at least one well defined peak, absorption spectroscopy at this precise wavelength produces accurate results. Without dissociation, the gas compound (e.g. NaOH) does not have such a highly wavelength specific absorption profile.

The location (i.e. wavelength) of the absorption peak of sodium depends on pressure. Moreover, the first part 520, as obtained by dissociating a molecule, has a large velocity, since part of the energy released in the dissociation is transformed to the kinetic energy of the first part. Therefore, the wavelength for the first part atom corresponding to the absorption peak may be slightly different from the values typically presented literature for the same atom, ion, molecule or radical, since the dissociation induced first part atom, ion, molecule or radical may have larger velocity than ambient similar dissociation product. Still further, depending on the energy of the dissociative light pulse 710 (or pulses), the first part 520 may be in an excited state. Therefore, the beam wavelength $\lambda_b$ may correspond to the absorption profile of the first part in the excited state. The beam wavelength $\lambda_b$ may correspond to the absorption profile of the first part in the ground state. The light source used to generate the light beam is preferably tunable such that the wavelength can be accurately tuned to correspond the absorption peak.

For the case of NaOH, the pulse wavelength $\lambda_{p1}$ is preferably from 300 nm to 340 nm, e.g. about 310 nm. Therefore the pulse light source may be selected from a wide range of light sources. In an embodiment, a pulse laser having a wavelength of 315 nm was used as the light pulse source. In another embodiment, a pulse laser having a wavelength of 330 nm was used as the light pulse source. The absorption spectrum of the sodium hydroxide molecule 510 shows a relatively high value for these specific wavelengths as depicted in FIG. 3*a*. It is further noted, that photons having this specific wavelength do not significantly dissociate other sodium compounds that may be present in the gas mixture, e.g. sodium chloride or other sodium halides.

The gas compound molecules are dissociated using at least one light pulse. The light pulse comprises photons of which energy is sufficient for dissociating at least some gas compound molecules. The light pulse may comprise photons having a wavelength of less than 430 nm. It is noted that the energy of a photon having this wavelength is 2.88 eV. Therefore, the light pulse 710 may comprise photons capable of exciting the compound molecules 510 to a dissociative state 512 having an energy of at least 2.88 eV above the ground state. However, referring to FIG. 2*b*, also photons having a longer wavelength are capable of exciting the compound molecules to a dissociative state having an energy on at least 2.88 eV above the ground state, provided that the gas compound molecule 510 is excited to the dissociative state 512 via an intermediate excited state 510*c* (energy state or virtual state) using at least two photons (515, 515*b*). The wavelengths of the at least one photon (515, 515*b*) may be selected such that the at least one photon is/are capable of exciting the gas compound molecule to a dissociative state having an energy of at least 2.88 eV above the ground state. The wavelength(s) of the photon(s) 515 or 515 and 515*b* are selected according to the exciting sequence. The exciting sequence refers to the required subsequent energy quanta, by which the compound molecules 510 are excited to the dissociative state 512.

The term "ground state" above may refer to a minimum energy state. The term "ground state" may refer to the state, wherein the gas compound molecules are before excitation or dissociation. The "ground state" in the measuring environment may be different from the "ground state" in another temperature. Moreover the "ground state" may refer to the state of the dissociated parts after dissociation.

The dissociation process is not sensitive to the wavelength, provided that the wavelength is short enough. However, the absorption spectrum of a gas compound molecule is indicative of a probability for a photon having a wavelength to be absorbed by the gas molecule. Thus, even if dissociation is not sensitive to the wavelength, dissociative photons having a wavelength may dissociate more molecules than the same number of dissociative photons having a different wavelength. Therefore, the light pulse is not necessarily monochromatic. However, the light pulse may be essentially monochromatic, whereby the light pulse may consist of photons having the same wavelength.

As discussed above, the method comprises detecting a first value indicative of a first intensity $I_{k0}$ of the attenuated light beam 175. The first value indicative of a first intensity, $I_{k0}$, of the attenuated light beam 175 may be e.g. the signal level of the photodetector 320 corresponding to the first intensity, $I_{k0}$. Other possibilities, e.g. averaging will be discussed below.

Figure 4A:
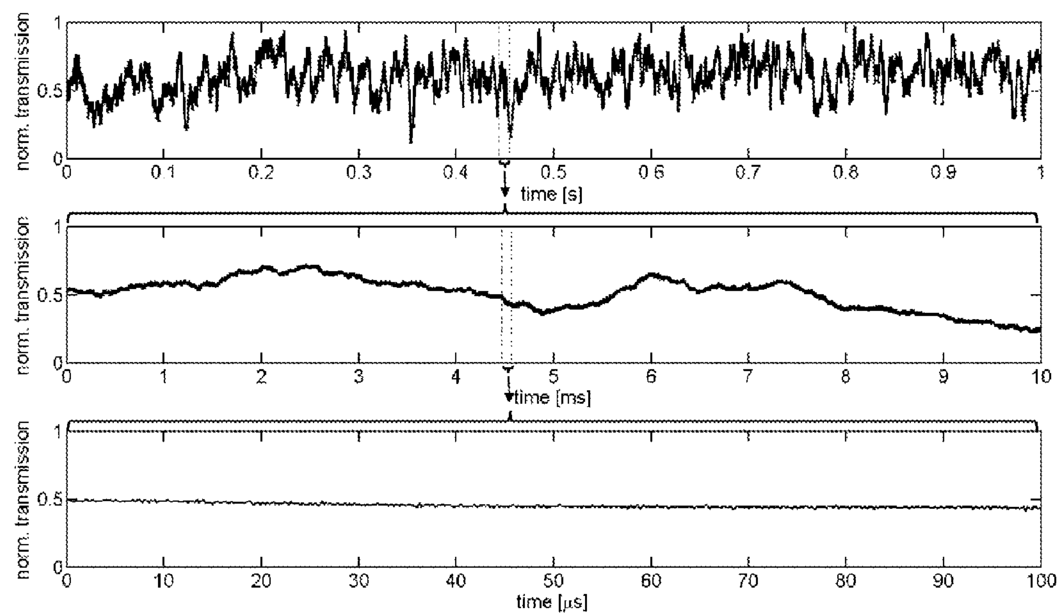
FIG. 4*a* shows a measurement signal obtainable from a device of any of the FIGS. 5*a*-5*c* in the time scale of one second, in the time scale of ten milliseconds, and in the time scale of hundred microseconds.

The gas mixture comprising the gas compound may be a result of a thermal process. In particular, the thermal process may be continuous, whereby the gas mixture may flow in a pipe, duct or channel. The gas mixture may comprise various amount of different gas compounds and liquid or solid particles. Therefore, the intensity of the attenuated light beam 175 fluctuates. The fluctuations tend to affect the accuracy of measurements. E.g. with absorption spectroscopy for flue gases, the flue gases may contain various amounts of solid particles travelling across the optical path 160, thereby affecting intensity of the attenuated light beam 175. Fluctuations are clearly seen in a time scale of the order of a second (s). FIG. 4*a* illustrates these fluctuations. In FIG. 4*a* the normalized intensity of the attenuated light beam 175 is shown for three time scales. First (topmost part) for a long time scale of 1 second, second (middle part) for an intermediate time scale of 10 milliseconds, and third (bottommost part) for a short time scale of 100 microseconds. In the longest time scale, the normalized signal fluctuates between about 0.2 and 1.0. In the intermediate time scale, the normalized signal fluctuates between about 0.2 and 0.7. In the short time scale, the normalized signal is practically constant (0.5). Thus it is seen that shortening the time scale for measurement decreases the fluctuations, and in this way increases the accuracy of the measurements. It is noted, that if the flow velocity of the flue gas is e.g. 10 m/s, the particles in the flue gas travel only 10 μm in a microsecond. Thus, if the size of the light beam is significantly larger than, say 10 μm, the fluctuations diminish. Therefore, a short time scale in combination with a relatively wide light beam diminishes fluctuations.

FIG. 4*a* shows the signal at the photodetector 320 (cf. e.g. FIG. 5*a* for the photodetector) in measurements, where the intensity of the light beam 170 is kept constant. In the figures, the signal of the photodetector 320 is proportional to the intensity of the attenuated light beam 175. In case the photodetector 320 has a nonlinear response, the intensity level may be deduced from the signal level using calibration information for the photodetector. FIG. 4*a* shows an intensity signal, as measured using a photodetector 320 in the different time scales as discussed above.

Figure 4B:
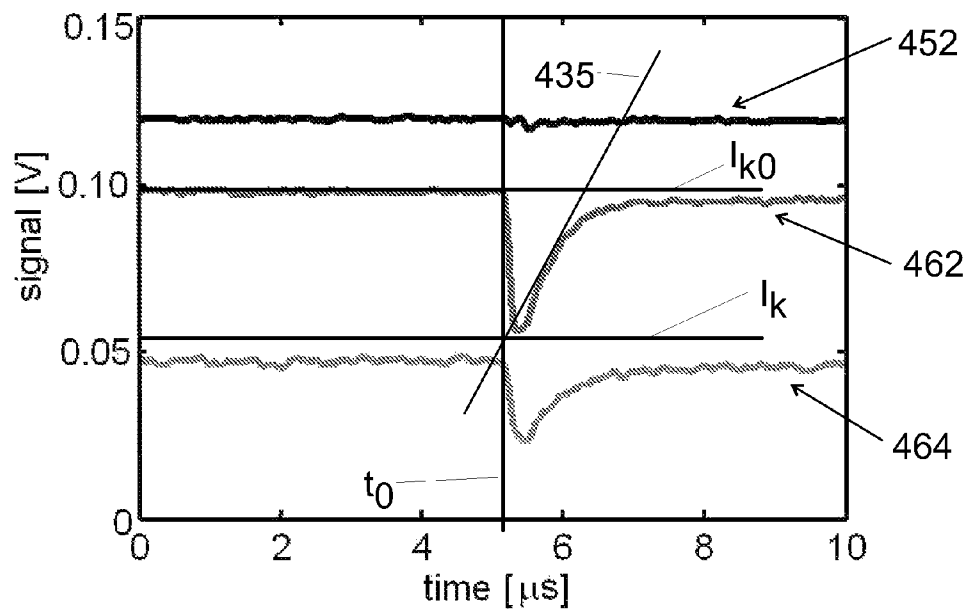
FIG. 4*b* shows actual measurement signals obtainable from a device of any of the FIGS. 5*a*-5*c* in a time scale of 10 micro seconds.
Figure 4C:
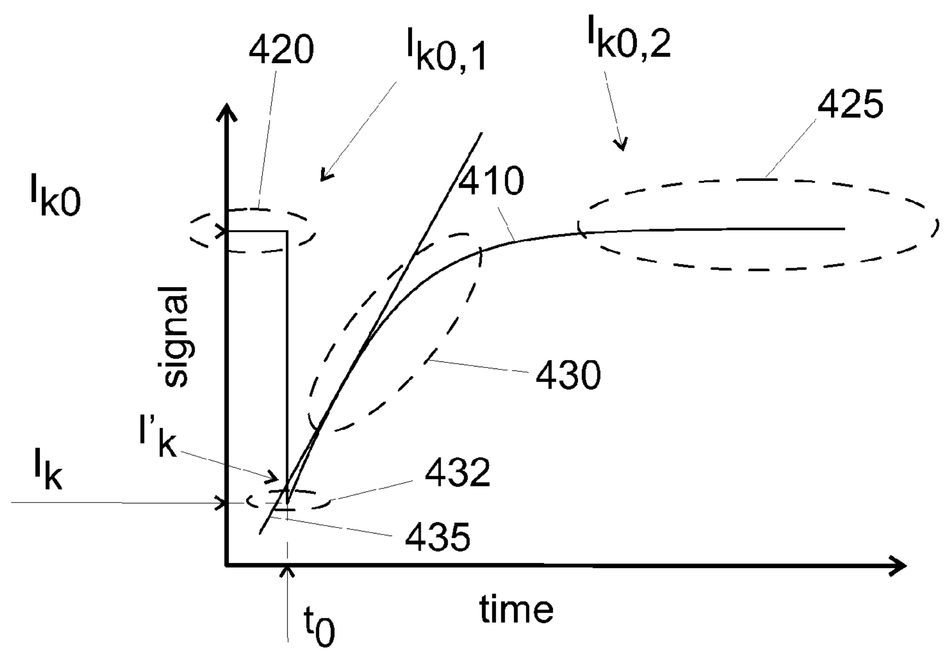
FIG. 4*c* shows an idealized measurement signal obtainable from a device of any of the FIGS. 5*a*-5*c*.

As discussed above, the beam 170 wavelength $\lambda_b$ is selected to so as to correspond to the absorption profile of the first part 520 (e.g. sodium atom) in the ground state or in an excited state. Thus, the dissociation shows in intensity of the attenuated light beam 175. Namely, the intensity decreases, corresponding to the amount of dissociated gas molecules (first parts 520) on the first optical path 160. This is shown in FIGS. 4*b* and 4*c*. The curves 462 and 464 in FIG. 4*b* and the curve 410 in FIG. 4*c* show measurements of the intensity of the attenuated light beam 175. The sharp drop in the intensity corresponds to dissociation, wherein the content of the dissociated first part 520 (e.g. sodium, cf. FIG. 2*a*) of the gas compound is rapidly increased. These first part atoms, molecules, ions, or radicals may move away from the first optical path e.g. with flue gases. Furthermore, the first part atoms, molecules, ions, or radicals may be highly reactive, especially with the (also dissociated) second parts (e.g. hydroxide molecule, FIG. 2*a*). Therefore, the first parts 520 rapidly react with other substances in the gas mixture, or move away from the first optical path 160, thereby increasing the intensity back to the original level, as shown in the FIGS. 4*b* and 4*c*.

Referring to FIG. 4*c*, the light pulse dissociates part of the gas compound molecules to the first part and the second part at the time $t_0$, which shows as a sharp drop in the curve 410. The signal returns to its initial level relatively rapidly. The time in which the signal returns to its original level is referred to as the recovery time. Referring to FIG. 4*b*, the recovery time may be of the order of 2 μs. The period, in which first part atoms or molecules are located on the first optical path 160, the first part having been produced by dissociating the gas compound molecules, is correspondingly referred to as the recovery period. The signal level before dissociating the gas molecules is denoted by $I_{k0}$, and the signal level immediately or essentially immediately after dissociating the gas molecules is denoted by $I_k$. The intensity $I_k$ may also correspond to a local minimum of the intensity signal. During the recovery period, the intensity of the attenuated light beam 175 has further decreased, as compared to the situation before the recovery period, due to the first parts of the gas molecule that are located on the first optical path 160.

The intensity signal before dissociating the gas molecules, $I_{k0,1}$, equals or approximately equals to the signal after a long time after dissociating the molecules, $I_{k0,2}$. In principle, the intensity $I_{k0}$ can be measured before the dissociative light pulse or after the light pulse and after the recovery time. However, as one technical advantage of the method is the short measurement time, preferably the intensity $I_{k0}$ is measured right before the dissociative light pulse.

The method comprises detecting a first value indicative of a first intensity $I_{k0}$ of the attenuated light beam 175. The first value indicative of the first intensity $I_{k0}$ may be e.g. an average of several measured signals. For example the first value may be an average of several measured signals before the dissociation, as shown in the FIG. 4c with the reference number 420. As another example, the first value may be an average of several measured signals a long time after the dissociation, as shown in the FIG. 4c with the reference number 425.

The method further comprises detecting a second value indicative of a second intensity $I_k$ of the attenuated light beam 175 during the recovery period, i.e. after dissociating at least part of the gas compound molecules 525 on the first optical path 160. The second value may be a local minimum value of the signal 410. The second value may be an average of several measured signals near the local minimum, as shown in the FIG. 4c with the reference number 432. It is also possible to fit a function to the measured data, particularly to the increasing part of the measured data. The increasing part of the measured data is shown in the FIG. 4c with the reference number 430. As an example of the function, a line 435 may be fitted to the data. The second value indicative of the second intensity $I_k$ of the attenuated light beam 175 may be detected using this function. In FIG. 4c, a possibility for the second value is denoted by $I'_k$. The value $I'_k$ is obtained as the value of the fitted function (the line 435) at the time $t_0$. Also other functions may be fitted to increasing part of the measured data, e.g. an exponential function or a polynomial.

The measured data may be filtered prior to detecting the first or the second value. For example, instead of the measured signal, a moving average of the signal may be used. Alternatively or in addition, outliers can be excluded from the measurements.

In order to characterize the time scales of the measurement, FIG. 4b shows the measured signals from a gas mixture resulting from a thermal process. A light pulse dissociates part of the gas compound molecules comprised in the flue gases at the time of about $t_0$=5 μs, which shows as a sharp drop in the curves 462 and 464. At the time t=7 μs, the signals are returned back to the initial level. Therefore, the time scale for these reactions is of the order of 2 μs. Moreover, the signal level seems to drop in approximately 200 ns. However, the signal level shown in FIG. 4b is filtered using a moving average. Therefore, the signal level seems to drop significantly slower than it actually does. The signal level drops in a time scale of the order of the duration of the light pulse 710. The second intensity $I_k$ of the attenuated light beam 175 may be measured from a local minimum of the intensity signal, or using a fitted function as discussed above.

The light beam 170 may also comprise light pulses. Thus, the light beam source 310 may be a pulse light source. When a pulse light source is used as the light beam source 310, the values at the photodetector 320 are detected when the attenuated light beam 175 illuminates the photodetector. Conversely, if light pulses are used as the light beam 170, the photodetector 320 detects periodically very small values corresponding to the times, when the attenuated light beam 175 is off. Relevant values for the method may be obtained when the attenuated light beam 175 illuminates the photodetector 320.

Having described the principle, it is apparent that the method further comprises:

- generating a light pulse 710, wherein the light pulse 710 comprises photons having a first pulse wavelength $\lambda_{p1}$,
- dissociating at least part of the gas molecules 510 or excited gas compound molecules (510b) on the first optical path 160 to a first part 520 and a second part 525, using the light pulse 710, whereby the light beam 170 is further attenuated to the attenuated light beam 175 by absorption to the first part 520 of the gas molecule 510 on the first optical path 160,
- detecting a second value indicative of a second intensity, $I_k$, of the attenuated light beam 175, and
- determining, using the first value and the second value, the content of the gas compound in the gas mixture.

More specifically, the method comprises

- detecting a second value indicative of a second intensity, $I_k$, of the attenuated light beam 175, wherein the attenuated light beam 175 is further attenuated by the first part 520 atoms, molecules, ions, or radicals on the first optical path 160.

The second value indicative of a second intensity, $I_k$, of the attenuated light beam 175 may be detected during the recovery period. Moreover, the second intensity, $I_k$, of the attenuated light beam 175 has been further attenuated by absorption of the light beam 170 to the dissociation induced first parts 520 on the first optical path 160. As only one type of light pulses 710 are used, the light pulse 710 can be considered the last light pulse, if necessary.

The second value indicative of a second intensity, $I_k$, of the attenuated light beam 175 may be e.g. the signal level of the photodetector 320 corresponding to the second intensity, $I_k$. The values indicative the intensities may naturally be the value of the intensities. A fitted function may be used such that a values of the signal in the increasing part of the measured data is indicative of the local intensity minimum or the second intensity, $I_k$. The photodetector may also be invertive, e.g. the signal may decrease even if the intensity increases. The increasing part of the measured data refers to increasing intensity.

FIG. 4b shows the first intensity $I_{k0}$ of the attenuated light beam 175 and the second intensity $I_k$ of the attenuated light beam 175 for the signal 462. The first intensity $I_{k0}$ refers to the intensity before dissociating at least part of the gas molecules 510 on the first optical path 160. The value indicative of the second intensity $I_k$ of the attenuated light beam 175 is determined using the function 435 (line), and the value for $I_k$ is determined as the value of the function at the time $t_0$ of the light pulse. The second intensity $I_k$ of the attenuated light beam 175 could be measured from a local minimum of the signal immediately or essentially immediately after dissociating the gas molecules.

It has previously been noticed that alkalihalides can be measured with a method, wherein the wavelengths are selected specifically for alkalihalide measurements. This has been disclosed in a non-public Finnish patent application FI20116232 (filed on Dec. 5, 2011), wherein a method for measuring alkalihalide content of flue gas was disclosed. Content of alkalihalides in flue gases is therefore beyond the scope of the present invention. With regard to alkalihalides, e.g. for potassium chloride, the pulse wavelength may be about $\lambda_{p1}$=266 nm, while the beam wavelength may be e.g. $\lambda_b$=766.515 nm±0.01 nm.

The term alkalihalide, in that application and in the present application, refers to a molecule of the type $MH^a$, wherein M is an alkali atom (metal), excluding hydrogen, from the group IA of periodic table of elements and $H^a$ is a halogen atom from the group VIIA of the periodic table of elements. Specifically, for an alkalihalide, the metal M can be selected from the group of Li, Na, K, Ru, Cs, and Fr, and the halogen $H^a$ can be selected from the group of F, Cl, Br, I, and At. Even more specifically M can be lithium, sodium or potassium, while $H^a$ can be chlorine or bromine.

In some embodiments, the pulse wavelength $\lambda_{p1}$ may be at most 430 nm. I.e. the set of wavelengths for the pulse wavelength $\lambda_{p1}$ comprises the wavelength 430 nm and all shorter wavelengths. To exclude alkalihalides from these measurements, in some embodiments the wavelengths 420 nm, 370 nm, and 270 nm may be excluded from the set of wavelengths for the pulse wavelength $\lambda_{p1}$. In some embodiments, in addition or alternatively, the wavelength 266 nm may be excluded from the set of wavelengths for the pulse wavelength $\lambda_{p1}$. In some embodiments, in addition or alternatively, the wavelength 270 nm may be excluded from the set of wavelengths for the pulse wavelength $\lambda_{p1}$. In some embodiments, in addition or alternatively, the wavelengths from 230 nm to 290 nm may be excluded from the set of wavelengths for the pulse wavelength $\lambda_{p1}$.

In some embodiments the beam wavelength $\lambda_b$ may be at most 1800 nm and the pulse wavelength $\lambda_{p1}$ may be at most 430 nm. I.e. the set of wavelengths for the beam wavelength $\lambda_b$ and the pulse wavelength $\lambda_{p1}$ comprises all the pairs ($\lambda_b{}^s$; $\lambda_{p1}{}^s$), wherein $\lambda_b{}^s \leq 1800$ nm and $\lambda_{p1}{}^s \leq 430$ nm. In some embodiments, the pair of wavelengths (766.515 nm; 266 nm) is excluded from the set of wavelengths for the beam wavelength and the pulse wavelength. In some embodiments, all the pairs of wavelengths ($\lambda_b{}^s$; 266 nm), wherein $\lambda_b{}^s$ is selected from the group of {766.515 nm, 770 nm, and 404 nm}, is excluded from the set of wavelengths for the beam wavelength and the pulse wavelength. In some embodiments, all the pairs of wavelengths ($\lambda_b{}^s$; $\lambda_{p1}{}^s$), wherein $\lambda_b{}^s$ is selected from the group of {766.515 nm, 770 nm, and 404 nm}, and $\lambda_{p1}{}^s$ is selected from the group from 230 nm to 290 nm, is excluded from the set of wavelengths for the beam wavelength and the pulse wavelength. In some embodiments, all the pairs of wavelengths ($\lambda_b{}^s$; 420 nm), wherein $\lambda_b{}^s$ is selected from the group of {766.515 nm, 770 nm, 404 nm, 589 nm, 330 nm, and 285 nm}, is excluded from the set of wavelengths for the beam wavelength and the pulse wavelength. In some embodiments, all the pairs of wavelengths ($\lambda_b{}^s$; 420 nm), wherein $\lambda_b{}^s \leq 1800$ nm, is excluded from the set of wavelengths for the beam wavelength and the pulse wavelength.

The gas mixture, from which the content of the gas compound is to be measured, may comprise many different gases. For example, the gas mixture may comprise alkalihydroxides and alkalihalides in gaseous form. The alkalihalide molecules may disturb the measurement of alkalihydroxides. For example, if the gas mixture comprises both sodium hydroxide and sodium chloride, the dissociation of both sodium hydroxide and sodium chloride to atomic sodium (and hydroxide or chlorine) increases the content of atomic sodium of the gas mixture. As the content of atomic sodium is detected by the light beam, it is not necessarily clear, whether the sodium atoms are the result of dissociation of NaOH or NaCl. Thus the content of the gaseous sodium hydroxide or sodium chloride remain unknown. Therefore, to specifically measure the content of the hydroxide, the method may comprise:

selecting the pulse wavelength $\lambda_{p1}$ such that at least part of the gas compound molecules (or at least part of the excited gas compound molecules; or at least part of a dissociated part 530, 534; or at least part of the excited dissociated part) are dissociated with the light pulse and no alkalihalide molecule is dissociated with the light pulse OR selecting the pulse wavelength $\lambda_{p1}$ and spectrum of wavelengths such that at least part of the gas compound molecules (or at least part of the excited gas compound molecules; or at least part of a dissociated part 530, 534; or at least part of the excited dissociated part) are dissociated with the light pulse and essentially no alkalihalide molecules are dissociated with the light pulse OR (i) selecting the pulse wavelength $\lambda_{p1}$ such that at least part of the gas compound molecules (or at least part of the excited gas compound molecules; or at least part of a dissociated part 530, 534; or at least part of the excited dissociated part) are dissociated and at least some alkalihalide molecules ($MH^a$) are dissociated with the light pulse and (ii) selecting the beam wavelength $\lambda_b$ of the light beam such that it does not correspond to and absorption peak of the alkali metal atom (M) dissociated by the light pulse. In this case the wavelength of the light beam may be selected such that it corresponds to an absorption peak of some other atom than the alkali metal atom (M). For example in case a potassium halide molecule and a sodium hydroxide molecule can be dissociated with the same pulse, the beam wavelength may be selected to correspond to the absorption peak of sodium. Thus the beam wavelength may be selected not to correspond an absorption peak of potassium.

The wavelength for the light pulse may be selected using the absorption spectrum of alkalihalide molecules, and/or using the absorption spectrum of a gas molecule, wherein the gas molecule is not an alkalihalide molecule, and/or using the price (or other) information on available light sources. The light pulse may be essentially coherent.

The term "essentially no alkalihalide molecules are dissociated" above means the case, where the light pulse dissociates both alkalihalides and other compounds, and the ratio of the number of dissociated alkalihalide molecules to the total number of dissociated molecules is small, preferably less than 10%. The wavelength and the spectrum of wavelengths may be selected according to the absorption cross sections of the gas molecules. For example, when sodium hydroxide (NaOH) is to be measured in the presence of sodium chloride (NaCl), the wavelength of the pulse may be selected using the information shown in FIG. 3*a*. FIG. 3*a* shows the normalized absorption cross section as function of wavelength for both NaOH and NaCl. As seen from FIG. 3*a*, when the pulse wavelength is about 310 nm, or the pulse comprises photons having the wavelength from 300 nm to 350 nm, the light pulse dissociates essentially no alkalihalide molecules, but dissociates the gas molecules. The pulse needs not to be generated by a laser, whereby the wavelength spectrum for the pulse may be wide.

In this case the selected ratio, 10%, represents a maximum for a systematic error in the measurements. However, it has also been noticed, that in typical thermal processes, the gas compound content may vary e.g. about 20% due to fluctuations in the feedstock, process temperature, process pressure, and/or other parameters. In this respect, 10% should be an acceptable maximum for systematic error. However, with reference to FIG. 3*a*, the pulse wavelength can often be selected also such that the ratio of the number of dissociated alkalihalide molecules to the total number of dissociated molecules is even smaller, e.g. less than 5%, or less than 1%.

The last case refers to the situation, where e.g. both potassium chloride molecules and sodium hydroxide molecules are dissociated with the same light pulse. In that case the beam wavelength may be selected to correspond to the sodium atom, whereby the potassium chloride molecules are not measured.

Referring further to FIG. 3*a* it is noted that if only sodium chloride molecules would have to be dissociated without dissociating sodium hydroxide molecules, a pulse wavelength of 277 nm could be used. However, dissociating an alkalihalide and also measuring the content of the corresponding alkali atom is beyond the applied scope of protection of the present application for the reasons discussed above.

It is also possible to detect the content of two different gas compound using a light pulse that dissociates molecules of a first gas compound and molecules of a second gas compound. Thus, the light pulse dissociates the molecules of the first gas compound to first first parts and to first second parts. Furthermore, the light pulse dissociates the molecules of the second gas compound to second first parts and to second second parts. As an example, a light pulse may dissociate both sodium hydroxide and potassium hydroxide molecules. The resulting first first part may refer to a sodium atom and the second first part may refer to a potassium atom. Both the first second part and the second second part refers in this case to the hydroxide molecule.

The wavelengths of the light beam 170 may be selected such that the light beam comprises photons corresponding to a first absorption peak of the first first part and further comprises photons corresponding to a second absorption peak of the second first part. E.g. the light beam may comprise photons corresponding to an absorption peak of sodium and further comprise photons corresponding to an absorption peak of potassium.

Thus the content of two different gas compounds may be measured with the method. This embodiment comprises

- generating a light beam 170, wherein the light beam 170 comprises photons having a first beam wavelength $\lambda_{b1}$ and photons having a second beam wavelength $\lambda_{b2}$,
- guiding the light beam 170 to a first optical path 160, wherein
- the first optical path 160 runs through a space 110 containing the gas mixture comprising the gas compounds, whereby the light beam 170 is attenuated to an attenuated light beam 175 and
- detecting a first value indicative of a first intensity $I_{k0}$ of the attenuated light beam 175 at the first beam wavelength $\lambda_{b1}$,
- detecting a third value indicative of a first intensity $I_{k0}$ of the attenuated light beam 175 at the second beam wavelength $\lambda_{b2}$,
- generating a light pulse 710, wherein the light pulse 710 comprises photons 515 having a first pulse wavelength $\lambda_{p1}$,
- dissociating at least part of (i) gas compound molecules or (ii) excited gas compound molecules on the first optical path 160 to first part atoms, molecules, ions, or radicals, and to another part using the light pulse 710, whereby the light beam 170 is further attenuated to an attenuated light beam 175 by absorption to the first part atoms, molecules, ions, or radicals on the first optical path 160,
- detecting a second value indicative of a second intensity $I_k$ of the attenuated light beam 175 at the first beam wavelength $\lambda_{b1}$,
- detecting a fourth value indicative of a second intensity $I_k$ of the attenuated light beam 175 at the second beam wavelength $\lambda_{b2}$,
- determining, using the first value and the second value, the content of a first gas compound content of the gas mixture, and
- determining, using the third value and the fourth value, the content of a second gas compound content of the gas mixture.

Alternatively to one light beam, two light beams may be used: A first light beam that comprises photons corresponding to a first absorption peak of the first first part; and a second light beam that comprises photons corresponding to a second absorption peak of the second first part.

Thus the content of two different gas compounds may be measured with the method. This embodiment comprises

- generating a first light beam 170, wherein the first light beam 170 comprises photons having a first beam wavelength $\lambda_{b1}$,
- generating a second light beam, wherein the second light beam comprises photons having a second beam wavelength $\lambda_{b2}$,
- guiding the light beams to a first optical path 160, wherein the first optical path 160 runs through a space 110 containing the gas mixture comprising the gas compounds, whereby the light beams are attenuated to attenuated light beams and
- detecting a first value indicative of a first intensity $I_{k0}$ of the attenuated first light beam 175,
- detecting a third value indicative of a first intensity $I_{k0}$ of the attenuated second light beam,
- generating a light pulse 710, wherein the light pulse 710 comprises photons 515 having a first pulse wavelength $\lambda_{p1}$,
- dissociating at least part of (i) gas compound molecules or (ii) excited gas compound molecules on the first optical path 160 to first part atoms, molecules, ions, or radicals, and to another part using the light pulse 710, whereby the light beams are further attenuated to attenuated light beams by absorption to the first part atoms, molecules, ions, or radicals on the first optical path 160,
- detecting a second value indicative of a second intensity $I_k$ of the attenuated first light beam 175,
- detecting a fourth value indicative of a second intensity $I_k$ of the attenuated second light beam,
- determining, using the first value and the second value, the content of a first gas compound content of the gas mixture, and
- determining, using the third value and the fourth value, the content of a second gas compound content of the gas mixture.

Still further, it is possible to detect the content of two different gas compounds using two light pulses such that the first light pulse dissociates molecules of a first gas compound and the second light pulse dissociates molecules of a second gas compound. Thus, the first light pulse dissociates the molecules of the first gas compound to first first parts and to first second parts. Furthermore, the second light pulse dissociates the molecules of the second gas compound to second first parts and to second second parts. As an example, a first light pulse may dissociate magnesium oxide MgO molecules and a second light pulse may dissociate magnesium sulfate $MgSO_4$ molecules. The resulting first first part may refer to a magnesium atom and the second first part may refer also to a magnesium atom. The first second part may refer to oxygen atom and the second second part may refer to a sulfate molecule.

In this case the light beam may comprise photons corresponding to the absorption peak of magnesium. However, by timing the two light pulses slightly differently, both magnesium oxide and magnesium sulphate may be measured with the method. This embodiment comprises

- generating a light beam 170, wherein the light beam 170 comprises photons having a beam wavelength $\lambda_b$
- guiding the light beam 170 to a first optical path 160, wherein
- the first optical path 160 runs through a space 110 containing the gas mixture comprising the gas compounds, whereby the light beam 170 is attenuated to an attenuated light beam 175 and detecting a first value indicative of a first intensity $I_{k0}$ of the attenuated light beam 175, generating a light pulse 710, wherein the light pulse 710 comprises photons 515 having a first pulse wavelength $\lambda_{p1}$, dissociating at least part of (i) gas compound molecules or (ii) excited gas compound molecules on the first optical path 160 to first part atoms, molecules, ions, or radicals, and to another part using the light pulse 710, whereby the light beam 170 is further attenuated to an attenuated light beam 175 by absorption to the first part atoms, molecules, ions, or radicals on the first optical path 160, detecting a second value indicative of a second intensity $I_k$ of the attenuated light beam 175, determining, using the first value and the second value, the content of a first gas compound content of the gas mixture, optionally detecting a third value indicative of an intensity $I_{k0}$ of the attenuated light beam 175, generating another light pulse, wherein the another light pulse comprises photons 515 having another pulse wavelength $\lambda_{p1,1}$, dissociating at least part of (i) second gas compound molecules or (ii) excited second gas compound molecules on the first optical path 160 using the another light pulse, whereby the light beam 170 is further attenuated to an attenuated light beam 175 by absorption dissociation product on the first optical path 160, detecting a fourth value indicative of a second intensity $I_k$ of the attenuated light beam 175, determining, using the fourth value and at least one of the first value and the third value, the content of the second gas compound content of the gas mixture.

In some cases the measurement conditions are stable, whereby the intensity of the attenuated light beam, $I_{k0}$, is essentially constant. In such stable conditions only one measurement of the intensity is sufficient. Thereby the content of the second gas compound content of the gas mixture may be determined using the fourth value and the first value. However, is the conditions are not sable, the intensity $I_{k0}$ fluctuates. In these conditions, the third value needs to be measured. Thereby the content of the second gas compound content of the gas mixture may be determined using the fourth value and the third value. Also, both the first and the third values may be used to describe the attenuated intensity $I_{k0}$. For example their average value can be used.

Gas molecules that can be measured using only one dissociative light pulse include alkali hydroxides of the form MOH, wherein M is an alkali atom (metal), excluding hydrogen, from the group IA of periodic table of elements; metal (mono)oxides, such as PbO, NiO, MnO, and CrO; thermally dissociated polyhalide metal salts, such as PbCl, HgCl; polyhalide salts of metals, such as $PbCl_2$; and nitrogen oxide $NO_2$. Moreover, the method can be applied for measurements of metal sulfides, wherein the metal sulfide has the form $M^1S$, wherein $M^1$ is a metal and S is a sulfur atom, for example PbS, ZnS, SnS, and CuS. Still further, other examples include carbonates, e.g. metal carbonates such as potassium carbonate ($K_2CO_3$) and sulfates, e.g. metal sulfates such as potassium sulfate ($K_2SO_4$). A single potassium atom may be dissociated from these compounds with a pulse. Still further, some polyhalides, e.g. $SCl_2$, $TeBr_2$, $PbBr_2$, and $PbI_2$ may be dissociated to an atom and to two halogen atoms with a single pulse.

It is understood that these gases are only examples, and the same principle can be applied to many other gases.

As for metal polyhalides, especially $PbCl_2$, the radical PbCl has absorption band at the deep ultraviolet, which poses some limitations for the light beam source. Another possibility for the measurement of $PbCl_2$ will be discussed below. Nitrogen oxide $NO_2$ may be dissociated to nitrogen (mono)oxide NO and oxygen atom O using a pulse wavelength from 250 nm to 410 nm. Nitrogen (mono)oxide NO has relatively strong absorption peaks in the wavelength range from 203 nm to 227 nm.

In an embodiment, the method is used to measure the content of a gas compound from a gas mixture, wherein the gas compound consists of gas compound molecules 510 comprising at least three atoms. In this embodiment, the method comprises dissociating a gas compound molecule 510 comprising at least three atoms.

Measuring Device, Single-Step Dissociation

Figure 5A:
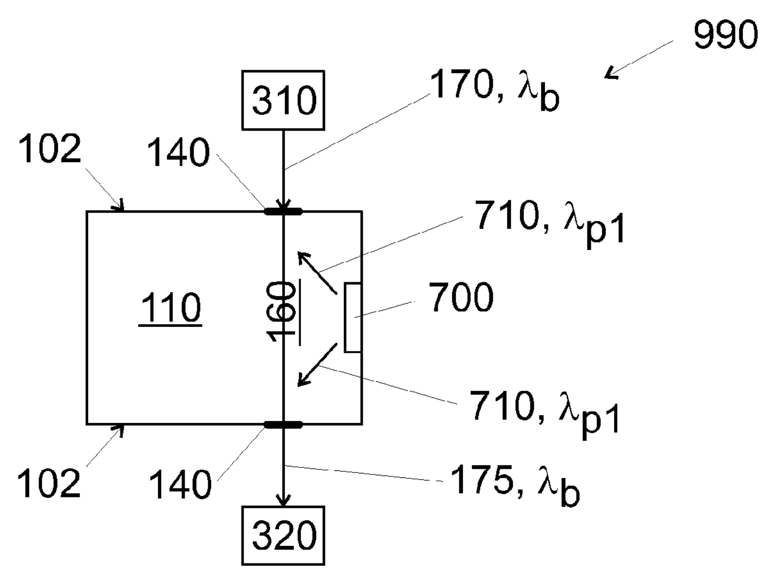
FIG. 5*a* shows a device for the measuring the content of a gas compound in a gas mixture.

FIG. 5*a* shows an embodiment of a device 990 for measuring the content of a gas compound in a gas mixture using one dissociative light pulse. The device comprises a light beam source 310. The light beam source 310 is arranged to generate light comprising photons having the beam wavelength $\lambda_b$. The light beam source 310 may produce a monochromatic or essentially monochromatic light beam 170. The light beam source 310 may produce a coherent or essentially coherent light beam 170. It is noted, that even if a laser is used as the light source 310, whereby the light beam 170 is essentially coherent, scattering from the particles in the flue gas in the space 110 widens the light beam in the space 110. As discussed above, the light beam source 310 may be arranged to generate light pulses.

As the content the gas compound is measured from the content of the first part 520 (FIG. 2*a*) of the gas molecule, wherein the first part 520 is generated by dissociation, the beam wavelength $\lambda_b$ of the light beam 170 is selected such that content of the first part can be measured. As the content is measured from the absorption, the gas compound content on the first optical path 160 becomes measured. The first optical path runs through the space 110 containing the gas mixture.

The light beam 170 has a cross section, and the cross section has a first dimension $I_1$ and a second dimension $I_2$, wherein the second dimension is perpendicular to the first dimension. The orientations for the dimensions are selected such that the first dimension is the smaller of the first and the second dimension, i.e. $I_1=\min(I_1,I_2)$. The dimensions may be equal, e.g. the beam may be circular. Theoretically there is no limit for the dimensions of the light beam 170. However, a narrow light beam expands more in the space 110 than a wide light beam. For example, turbulence in the space 110 affects the temperature distribution in the optical path, thereby affecting the refraction coefficient for light and further affecting the travel of the light beam. Moreover, a very wide light beam may diminish the sensitivity of the method. The first dimension of the light beam may be e.g. in the range from 1 mm to 100 mm. The first dimension $I_1$ of the light beam is preferably from 20 mm to 50 mm. In some embodiments of the invention the light beam 170 has an essentially circular cross-section. In these embodiments, the radius of the light beam 170 is preferably in the range from 10 mm to 25 mm.

The device 990 of FIG. 5*a* further comprises a light pulse source 700. The light pulse source is arranged to emit light pulses 710 comprising high energy photons 515 (FIG. 2*a*) such that at least some of the photons dissociate the gas molecules or the excited gas molecules on the first optical path 160. The light pulse source 700 may be arranged to emit light pulses 710 comprising photons having a wavelength $\lambda_{p1}$, wherein $\lambda_{p1}$ is short enough for dissociating the gas molecules 510 (FIG. 2*a*). The light pulses dissociate at least part of the gas molecules to a first part and a second part, as discussed above. At least part of the light pulses are guided to the first optical path 160. As light pulse 710 or a part of the light pulse 710 travels across the first optical path 160, at least part of the gas molecules 510 (FIG. 2*a*) on the first optical path 160 are being dissociated to the first part 520 and the second part 525.

In the embodiment of FIG. 5*a*, the light pulse source 700 may be e.g. a Xenon flash source. The light pulse 710 may be emitted to substantially all angles to the space 110 at the same time.

The device 990 further comprises a photodetector 320. The photodetector is arranged to detect the intensity of the attenuated light beam 175. The attenuated light beam comprises photos having the wavelength $\lambda_b$.

In the embodiment of FIG. 5*a*, the light beam source 310, the light pulse source 710, and the photodetector 320 are located in the exterior of the space 110, i.e. outside of the walls 102. However, in another embodiment, at least one of the components is located in the interior of the space 110, e.g. to detect gas compounds of the ambient.

Figure 5B:
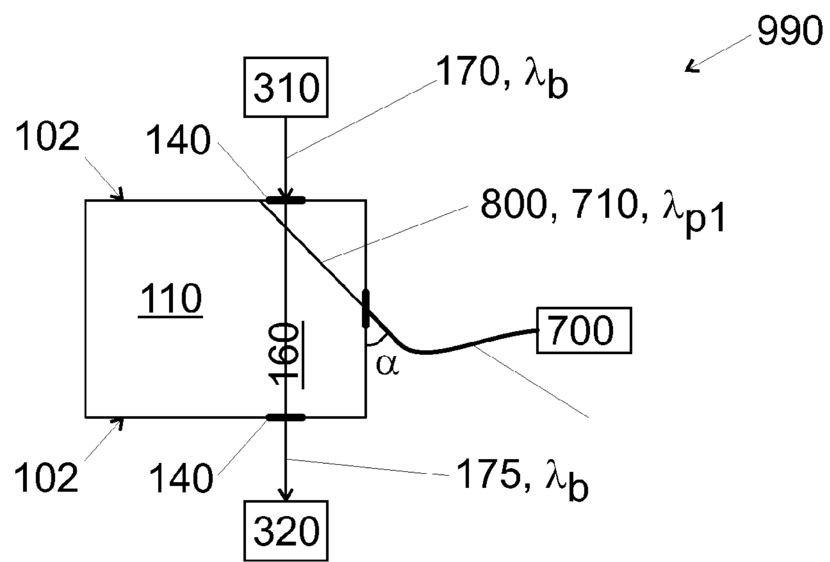
FIG. 5*b* shows another device for the measuring the content of a gas compound in a gas mixture.

FIG. 5*b* shows another embodiment of the device. In FIG. 5*b*, the light pulse 710 is guided to a second optical path 800. The second optical path 800 crosses the first optical path 160. Moreover, the angle of the light pulse, α, is adjustable. Therefore, the angle α defines the position at which the second optical path 800 crosses the first optical path 160. Thus, the method becomes position sensitive. In the embodiment, the gas molecules are dissociated on the second optical path 800. However, the dissociation affects the intensity of the attenuated light beam 175 only in the case that the gas molecules are dissociated also on the first optical path 160. Therefore, the first part content becomes measured from the volume, where the second optical path 800 crosses the first optical path 160. As the angle α is adjustable, first part content in all positions at the first optical path 160 may be measured. It is also possible to make position sensitive measurements using essentially perpendicular optical paths 160 and 800 and using a movable light pulse source.

Figure 5C:
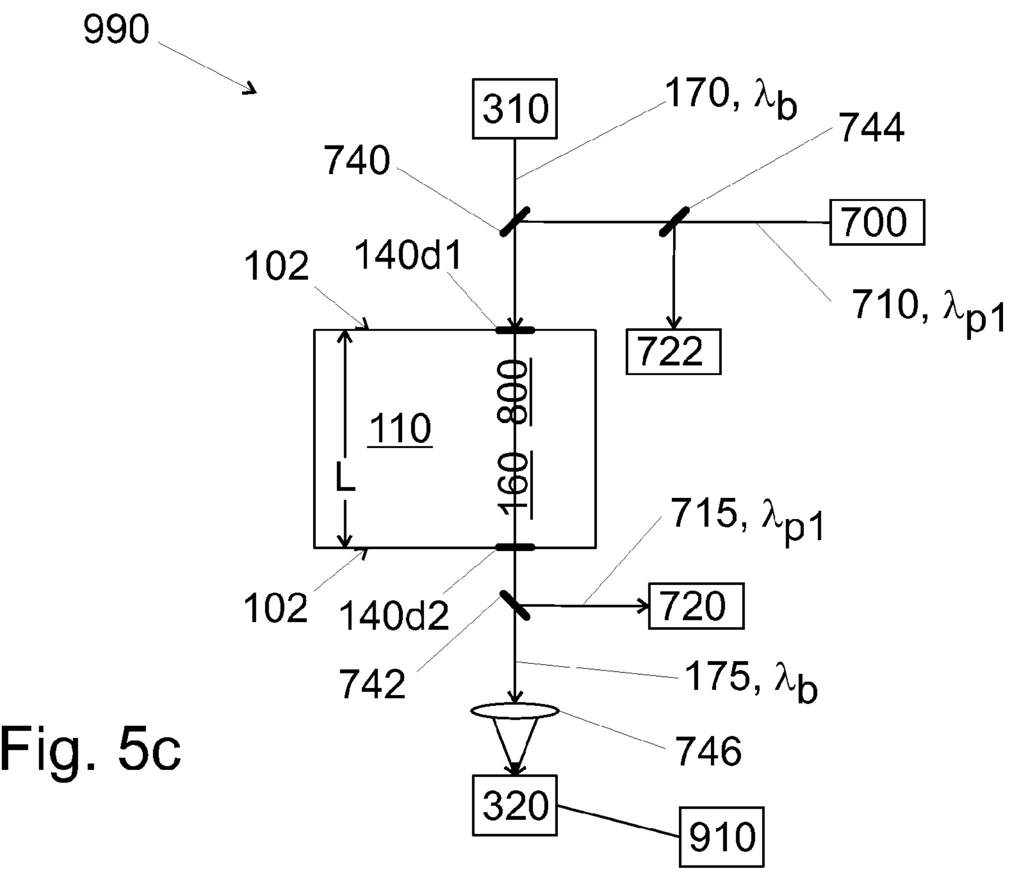
FIG. 5*c* shows another device for the measuring the content of a gas compound in a gas mixture.

FIG. 5*c* shows a preferred embodiment of the invention using one light pulse to dissociate a gas molecule. The device 990 of FIG. 5*c* comprises:

- a light beam source 310, arranged to emit a monochromatic and coherent light beam 170 having the beam wavelength $\lambda_b$,
- a light pulse source 700, arranged to emit a monochromatic and coherent light pulse 710 having the pulse wavelength $\lambda_{p1}$,
- a first optical element 740, arranged to guide
  - the light beam 170 to a first optical path 160 and
  - the light pulse 710 to a second optical path 800 such that the second optical path 800 overlaps the first optical path 160,
- a second optical element 742, arranged to pass the attenuated light beam 175, i.e. light having the wavelength $\lambda_b$, and to deflect, reflect, or absorb the attenuated light pulse 715, i.e. light having the wavelength $\lambda_{p1}$,
- a third optical element 744, arranged to reflect a first part of light having the wavelength $\lambda_{p1}$ and to pass a second part of light having the wavelength $\lambda_{p1}$,
- a first photodetector 320, arranged to detect the intensity of the attenuated light beam 175 having the wavelength $\lambda_b$,
- a lens 746, arranged to converge the attenuated light beam 175 to the first photodetector 320,
- a second photodetector 720, arranged to detect the intensity of attenuated light pulse 715, the attenuated light pulse having the wavelength $\lambda_{p1}$,
- a third photodetector 722, arranged to detect the intensity of light having the wavelength $\lambda_{p1}$, and
- a data processing unit 910, wherein the data processing unit is arranged to calculate the gas compound content in the gas mixture using a first value, the first value being indicative of a first intensity $I_{k0}$ of the attenuated light beam 175 on the photodetector 320, and a second value, the second value being indicative of a second intensity $I_k$ of the attenuated light beam 175 on the photodetector 320.

FIG. 5*c* also shows, even though not components of the device 990,

- walls 102 defining a space 110 in their interior, the space 110 arranged to contain the gas mixture,
- a first window 140*d*1, arranged to pass the light pulse 710 and the light beam 170 to the space 110 and to retain gas mixture within the space 110, and
- a second window 140*d*2, arranged to pass the light pulse 710 and the light beam 170 from the space 110 and to retain the gas mixture within the space 110.

It is noted, that the intensity or the energy of the attenuated light pulse 715 is not necessarily measured, and therefore, the second photodetector 720 may be omitted. The third optical element 744 and the third photodetector 722 are arranged to measure the intensity or energy of the light pulse 710. The intensity or the energy of the light pulse 710 is not necessarily measured, and therefore, the third photodetector 722 and the third optical element 744 may be omitted. In addition, the device may comprise other optical elements such as lenses to converge the first part of the light pulse 710 to the third photodetector, or the attenuated light pulse 715 to the second photodetector. Other examples of such optical elements of optical waveguides, e.g. optical fibres, arranged to guide light and/or to affect an angle or a position of a light beam or light pulse.

As described above, the second optical path 800 overlaps the first optical path 160. Referring to FIG. 5*c*, the second optical path 800 overlaps the first optical path 160 for example when the optical paths are essentially parallel and co-centric. The optical paths may also be essentially parallel, but the central axes may be shifted with respect to each other. The term essentially parallel may be interpreted such that the first optical path 160 is essentially parallel to the second optical path 800 if

- the optical paths are parallel, or
- the optical paths are so aligned, that the light beam 170 and the light pulse 710 at least partially overlap on all points between
  - a starting point, wherein the starting point is one of the first optical element 740 and the light beam source 310, whichever is comprised by the device and
  - an ending point, wherein the ending point is one of the second optical outlet 140*d*2, the optical element 742, the lens 746, and the first photodetector 320, whichever is comprised by the device, wherein
  - the components defining the starting and ending points are selected such that the length between the starting point and the ending point is the shortest of the different possibilities, or
- the angle between the central axis of the first optical path 160 and the central axis of the second optical path is less than 5 degrees.

The term "at least partially overlap on all points" is to be understood in the following way: the point (that is referred to) is a point of the central axis of the first optical path. Conversely, the central axis of the first optical path defines a set of points. As light travels in a straight manner, the central axis defines a plane that is perpendicular to the central axis. In this plane, the first optical path 160 defines a first cross sectional area, i.e. a first set of points. In this plane, the second optical path 180 defines a second cross sectional area, i.e. a second set of points. The optical paths partially overlap, with respect to this point and plane, when the first set of points comprise at least part of the points of the second set of points. The shortest of the possible paths is selected as discussed above, since (referring to FIG. 5*c*) evidently the beam and the pulse do not overlap before e.g. the optical element 740.

The cross section of the light beam and the light pulse is understood as follows. The intensity of the light beam typically has a maximum at the central axis of the light beam, and the intensity decreases as the distance from the central axis increases. Typically the decrement is exponential. The light beam is assumed to be located in the points, wherein the intensity is at least 1/e of the maximum intensity. 1/e is about 37%. From this, the cross section of the light beam be determined. The intensity of the light pulse typically has a maximum at the central axis of the light pulse, and the intensity decreases as the distance from the central axis increases. Typically the decrement is exponential. From this, the cross section of the light pulse be determined. The intensity profile may also have a different form, e.g. the intensity profile may comprise multiple peaks. Moreover, an intensity peak is not necessarily located at the central axis.

The light beam 170 may have a first radius $r_1$ from 0.5 mm to 50 mm. The light pulse 710 may also be coherent and have a cross-section. The cross section of the light pulse has a first dimension $d_1$ and a second dimension $d_2$, wherein the second dimension is perpendicular to the first dimension. The orientations for the dimensions are selected such that the first dimension is the smaller of the first and the second dimension, i.e. $d_1=\min(d_1,d_2)$. The dimension first may be equal to the second. Theoretically there is no limit for the dimensions of the light pulse 710. However, as will be seen, the dimensions of the light pulse affect the sensitivity of the method. The method is more sensitive if a narrow light pulse 710 is used. Moreover, a very wide light pulse may be hard to generate. The first dimension of the light pulse may be e.g. in the range from 1 mm to 100 mm. The first dimension of the light pulse is preferably from 20 mm to 50 mm. More preferably, the cross section of the light pulse 710 is greater than the cross section of the light beam 170, such that the light pulse 710, when present, surrounds the light beam 170. The light pulse 710 may have a circular cross section, whereby the light pulse may have a second radius $r_2$ from 0.5 mm to 50 mm. The first and the second radii may also be equal or approximately equal. Preferably the radius of the light pulse, $r_2$, is 1 mm-2 mm greater than the radius of the light beam, $r_1$. Preferably the intensity profile of the light pulse 710 is spatially uniform. The term spatially uniform refers to an intensity profile that is uniform on the cross sectional area of the pulse. The cross sectional area refers to the area of the cross section of the pulse, as defined above in the context of the term at least partly overlapping. The term uniform as such refers to a distribution that has essentially only a single value. (Naturally the intensity outside of the beam is zero). The spatially uniform intensity simplifies the calculations of the gas compound content. Typically the intensity profile of the light pulse 710 spatially decreases exponentially with the distance from the central axis of the light pulse 710. In these cases the cross sectional area refers to the area of the cross section of the pulse, wherein the pulse is considered to be located in the points, wherein the intensity of the pulse is at least 1/e of the maximum intensity. Here 1/e is about 37%. For the calculations of the gas compound content, the exponentially decreasing intensity is reasonably uniform. The intensity profile may also have a different form, e.g. the intensity profile may comprise multiple peaks. Moreover, an intensity peak is not necessarily located at the central axis. In case the intensity profile differs significantly from uniform, an effective area may be used e.g. in the equation 4 (to be presented later). Thus, instead of $A_p$ in the ratio $A_p/E_{0p1}$, the effective area may be used to take into account the intensity variations.

The central axis of the first optical path 160 may be shifted with respect to the central axis of the second optical path 800 by a distance d. The distance should be smaller than the sum of the radii, i.e. $d<r_1+r_2$. Preferable the distance should be smaller than the smaller of the radii, i.e. $d<\min(r_1,r_2)$. The optical paths 160, 800 are considered essentially co-centric, if the distance between the central axes of the optical paths 160, 800 is less 25% of the smaller of the following: smaller dimension of the light beam 170 and smaller dimension of light pulse 710. E.g. the optical paths 160, 800 are considered essentially co-centric, if the distance between the central axes of the optical paths 160, 800 is less than $0.25\times\min(2r_1,2r_2)$. The distance between the optical paths 160, 800 may be considered the minimum distance between the central axes of the optical paths 160, 800. Co-centric optical paths are essentially co-centric. The optical paths 160, 800 may be essentially co-centric, if they are essentially parallel.

In case the central axes of the optical paths are shifted with respect to each other, or in the case where there is an angle between the central axes of the optical paths, it may be possible to omit the second optical element 742 from the device. In this case it may be possible to locate the first photodetector 320 such that the attenuated light pulse 715 bypasses the first photodetector 320, and the attenuated light beam 175 hits the first photodetector 320.

The light pulse source 700 may be e.g. one of a pulse laser,
a Xenon flash source,
a continuous laser with a chopper,
a continuous laser operated in pulse mode,
a light emitting diode (LED) operated in pulse mode,
a continuous LED with a chopper,
a continuous light source operated in pulse mode, and
a continuous light source with a chopper.

Some light sources may be operated in a pulse mode using pulse mode drive current. A chopper may comprise e.g. a rotating opaque disk, the disk comprising a slit arranged to pass light through the slit. When light is directed towards the disk, a light pulse is generated when the light passes the slit of the otherwise opaque disk.

The duration of the light pulse is preferably less than the recovery time of the alkali atoms, which may be of the order of 2 μs or longer. Preferably the duration of the light pulse is short, e.g. at most 100 ns; more preferably at most 10 ns; and even more preferably at most 1 ns. The duration of the light pulse may be selected according to the light source. E.g. a pulse laser has typically a pulse duration from 1 fs ($10^{-15}$ s) to 100 ns ($100\times10^{-9}$ s). Lasers emitting very short pulses are typically mode locked, and may emit series of pulses instead of single light pulses. A Xenon flash may have a pulse duration of the order of 1 μs. The time between subsequent pulses, i.e. the time between the end of a pulse and the beginning of a subsequent pulse, is preferably significantly more than the recovery time of the parts of the gas, which may be of the order of 2 μs. However, the recovery time depends on the gas compound to be measured, and on the environment. For example, the lifetime of lead (to be presented later) is very short, whereby the recovery time may be only a few ns. The time between subsequent pulses is not necessarily more than the recovery time of the parts of the gas molecules. In an embodiment, the time between subsequent pulses was 1 s. The time between subsequent pulses need not to be more than the recovery time. In case a pulse is emitted during the recovery period, this affect the attenuated intensity $I_{k0}$, which in that case is slightly attenuated also due to the first part atoms, molecules, ions, or radicals on the optical path due to the previous dissociative light pulse.

The first optical element 740 is arranged to guide the light beam 170 to a first optical path 160 and the light pulse 710 to a second optical path 800 such that the second optical path 800 overlaps the first optical path 160. The first optical element 740 may be e.g. a wavelength-selective reflector that operates as a mirror for the wavelength $\lambda_{p1}$ and as a transparent object for the wavelength $\lambda_b$, as shown in the FIG. 5*c*. In a different configuration, the first optical element 740 could reflect light having a long wavelength and pass light having a short wavelength. The first optical element may be selected from a variety of known optical elements. For example, a prism or a grating may also operate as a wavelength-selective reflector. A fiber coupler may also operate as the first optical element.

The second optical element 742 is arranged to pass the attenuated light beam 175 and to deflect, reflect, or absorb the attenuated light pulse 715. The second optical element 742 is arranged to pass light having the wavelength $\lambda_b$ to the photodetector 320. The second optical element 742 is also arranged to prevent the attenuated light pulse 715 from entering the photodetector 320. The second optical element 742 may be any one of those that can be used as the first optical element 740. The second optical element may also be a filter arranged to absorb light having the wavelength $\lambda_{p1}$. In this case the device does not comprise the second photodetector 720.

The third optical element 744 is arranged to reflect a known (small) first part of light that hits the surface of the third optical element 744, and to pass a second part of the light. Thus, by measuring the intensity (or energy) of the reflected first part of the light pulse 710 using the third photodetector 722, the intensity (or energy) of the second part of the light pulse 710 may be calculated.

Referring to FIGS. 2*a*, 4*c* and 5*c*, a first intensity $I_{k0}$ of the of the attenuated light beam 175 is measured with the photodetector 320 before a light pulse 710 is emitted. In addition, after dissociating at least part of the gas molecules 525 on the first optical path 160 with the light pulse 710, a second intensity $I_k$ of the attenuated light beam 175 is detected. The light beam 170 is attenuated, among other things, to the attenuated light beam 175 by the absorption of the first part 520 atoms, molecules, ions, or radicals.

As the light pulse 710 or light beam 170 are not necessarily monochromatic, and all the components shown in FIG. 5*c* are not necessary to carry out the method, a device 990 for measuring the content of a gas compound in a gas mixture comprises:

- a light beam source 310, arranged to emit a light beam 170 comprising photons having a beam wavelength $\lambda_b$,
- a photodetector 320, arranged to detect the intensity of an attenuated light beam 175, wherein
  - a first optical path 160 is located between the photodetector 320 and the light beam source 310,
  - the first optical path 160 runs through a space 110 arranged to contain the gas mixture, and
  - the light beam 170 is arranged to be attenuated to the attenuated light beam 175 within the space 110, and the device further comprises

- a light pulse source 700, wherein
  - the light pulse source 700 is arranged to generate a light pulse 710 comprising photons having a second wavelength $\lambda_{p1}$, at least part of the photons dissociating at least part of (i) the gas molecules 510 or (ii) the excited gas molecules 510*b* on the first optical path 160 to a first part 520 and a second part 525, and
- the photodetector 320 is arranged to detect, during a recovery period, a second value indicative of a second intensity $I_k$ of the attenuated light beam 175, wherein the light beam 170 is further attenuated to the attenuated light beam 175 by absorption to the first part atoms or molecules on the first optical path 160.

The gas content may be calculated in a data processing 910 unit that receives a first value, the first value being indicative of a first intensity $I_{k0}$ of the attenuated light beam 175 on the photodetector 320 and a second value, the second value being indicative of a second intensity $I_k$ of the attenuated light beam 175 on the photodetector 320. The data processing unit 910 may be comprised in the device 990 for measuring the gas content. In case the data processing unit is located far apart from the photodetector 320, the device 990 may be relatively large is size. Thus, the device 990 may further comprise

- a data processing unit 910, wherein the data processing unit is arranged to calculate the gas content using a first value, the first value being indicative of a first intensity ($I_{k0}$) of the attenuated light beam (175) on the photodetector (320), and a second value, the second value being indicative of a second intensity ($I_k$) of the attenuated light beam (175) on the photodetector (320).

The device 990 may be arranged to measure the content of a gas compound in the gas mixture, wherein the gas compound is not an alkalihalide. Therefore, the device may be arranged to measure the content of a gas compound from a gas mixture, wherein the gas compound consists of gas compound molecules 510, and the gas compound molecule is not an alkalihalide molecule, wherein the alkalihalide molecule has form $MH^a$, wherein M is an alkali metal atom from the group of Li, Na, K, Ru, Cs, and Fr, and $H^a$ is a halogen atom from the group of F, Cl, Br, I, and At. The device may be such arranged by a proper selection of the wavelengths, as discussed above. Thus, the light beam source 310 or the light beam source 310 and the light pulse source 700 in combination are arranged to emit light a light pulse or a light pulse and a light beam, wherein the wavelength of the pulse or the pulse and the beam are selected such that

- at least part of the gas compound molecules are dissociated with the light pulse 710 and no alkalihalide molecule is dissociated with the light pulse 710 or
- at least part of the gas compound molecules are dissociated with the light pulse 710 and essentially no alkalihalide molecules are dissociated with the light pulse or (a) at least part of the gas compound molecules are dissociated with the light pulse 710 and at least some alkalihalide molecules ($MH^a$) are dissociated with the light pulse and (b) the wavelength of the light beam is selected such that it does not correspond to and absorption peak of the alkali metal atom (M) resulting from the dissociation of an alkalihalide molecule.

Moreover, the wavelengths of the device may be selected so as not to conflict with prior art. These wavelength were discussed in detail above in context with the method.

Still further, the light pulse may be arranged to dissociate a gas compound molecule, wherein the gas compound molecule is not an alkalihalide. Still further, the light pulse may be arranged to dissociate a gas compound molecule, wherein the gas compound molecule comprises at least three atoms.

Even if not shown in the FIGS. 5*a*-5*c*, the device may comprise a light beam source arranged to emit light comprising photons having a first beam wavelength $\lambda_{b1}$ and photons having a second beam wavelength $\lambda_{b2}$. The first beam wavelength may correspond to an absorption peak of a first gas compound. The second beam wavelength may correspond to an absorption peak of a second gas compound.

The device 990 may comprise a photodetector 320 that is arranged to measure the intensity of the attenuated, or further attenuated, light beam at two different wavelengths. These wavelengths may correspond to the first beam wavelength $\lambda_{b1}$ and to the second beam wavelength $\lambda_{b2}$. The values indicative of the intensity at first beam wavelength $\lambda_{b1}$ may be the first and second values, as discussed in the context of the method. The values indicative of the intensity at the second beam wavelength $\lambda_{b2}$ may be the third and fourth values, as discussed in the context of the method.

The device 990 may comprise two photodetectors, wherein the first of these two photodetectors is arranged to measure the intensity of the attenuated, or further attenuated, light beam at the first beam wavelength $\lambda_{b1}$, and the second of these two photodetectors is arranged to measure the intensity of the attenuated, or further attenuated, light beam at the second beam wavelength $\lambda_{b2}$ The values indicative of the intensity at first beam wavelength $\lambda_{b1}$ may be the first and second values, as discussed in the context of the method. The values indicative of the intensity at the second beam wavelength $\lambda_{b2}$ may be the third and fourth values, as discussed in the context of the method.

Alternatively, even if not shown in the FIGS. 5*a*-5*c*, the device may comprise another light beam source arranged to emit light comprising photons having a second beam wavelength $\lambda_{b2}$. The beam wavelength $\lambda_b$, as discussed in context of FIGS. 5*a* to 5*c*, may correspond to an absorption peak of a first gas compound. The second beam wavelength $\lambda_{b2}$ may correspond to an absorption peak of a second gas compound. These issues were also discussed in connection with the method.

The device 990 may comprise a photodetector 320 that is arranged to measure the intensity of the attenuated, or further attenuated, first and second light beams. The values indicative of the intensity of the attenuated first light beam may be the first and second values, as discussed in the context of the method. The values indicative of the intensity of the attenuated second light beam wavelength may be the third and fourth values, as discussed in the context of the method.

The device 990 may comprise two photodetectors, wherein the first of these two photodetectors is arranged to measure the intensity of the attenuated, or further attenuated, first light beam and the second of these two photodetectors is arranged to measure the intensity of the attenuated, or further attenuated, second light beam. The values indicative of the intensity of the attenuated first light beam may be the first and second values, as discussed in the context of the method. The values indicative of the intensity of the attenuated second light beam wavelength may be the third and fourth values, as discussed in the context of the method.

The device 990 may further comprise another light pulse source or other means for forming another light pulse. The another light pulse source may be arranged to emit the another light pulse comprising photons 515 having the another pulse wavelength $\lambda_{p1,1}$. The another pulse may be used to dissociate a second gas compound molecule, as discussed in the context of the method.

Moreover, if two photon excitation or multiple photon excitation is used to dissociate the gas molecule (FIG. 2*b*), the device may comprise means for forming another light pulse, such that at least part of photons of the other light pulse are arranged to excite the gas molecule to an excited gas molecule or
excite a dissociated part to an excited dissociated part.

The means for forming another light pulse may comprise a light pulse divider and a light pulse delayer. The means for forming another light pulse may comprise a light pulse source. A light pulse source, as discussed in connection with the first light pulse source, may be used the light pulse source for exciting the gas molecules or the excited parts One advantage of the method is that the first optical path 160 (and possibly also the second optical path 800) may extend through a gas line (pipe, duct, channel), from one wall 102*a*1 to an opposite wall 102*a*2, as depicted in FIG. 1*a*. Therefore, the gas content can be measured in situ from the first optical path 160. Thus, the problem of collecting a representative sample of the gas mixture for the measurements can be sidestepped simply by omitting sampling.

Gas Content, Single-Step Dissociation

In the following, the light pulse is assumed to be monochromatic or essentially monochromatic. In the following, the gas compound molecule 510 is assumed to be excited to the dissociative state 512 with a single photon 515 (FIG. 2*a*). In the following, the light beam is assumed to be monochromatic or essentially monochromatic. From the attenuated intensities $I_{k0}$ and $I_k$, the calculation of the content of the gas compound in the gas mixture may be done as follows:

The intensity of the light beam 170 is decreased in the space 110 by at least one of (i) absorption due to first part atoms, molecules, ions, or radicals produced in the dissociation of gas molecules using the light pulse 710, (ii) other processes such as scattering or absorption by other compounds or particles, and (iii) absorption due to other first part atoms, molecules, ions, or radicals produced by other dissociation processes of the gas molecules, e.g. produced by thermal dissociation.

Therefore, for the measured intensity before dissociation of gas molecules, one may write $I_{k0}=\phi I_0$, wherein $I_{k0}$ is the observed intensity of the attenuated light beam 175 before dissociation, $I_0$ is the intensity of the light beam 170 before entering the space 110, and $\phi$ is an attenuation factor. The attenuation factor $\phi$ takes into account attenuation of light beam due to the processes (ii) and (iii) above. The Beer-Lambert law may be applied to describe absorption by dissociated first part atoms or molecules. Therefore, for the intensity after the dissociation, one may write:

$$I_k = \varphi \exp\left(-\xi_M \frac{N}{V} \sigma_M L\right) I_0 = I_{k0} \exp\left(-\xi_M \frac{N}{V} \sigma_M L\right) \quad (1)$$

wherein $I_k$ is the intensity of the attenuated light beam 175 after the dissociation of the gas molecules by the light pulse 710, $I_{k0}$ is the intensity before the dissociation, $\xi_M$ is the first part content (as measured in proportion, e.g. in ppm or ppb; subscript M stands for metal, the gas molecule may be e.g. a metal hydroxide), N is the total number of atoms and molecules in a volume V, and $\sigma_M$ is the absorption cross section of the first part atom or molecule for the light beam having wavelength $\lambda_b$. The volume V refers to the volume on the first optical path 160 where dissociation takes place, and N refers to the total number of atoms and molecules within this volume. L is the distance, wherein absorption of light having the wavelength $\lambda_b$ to first part atoms or molecules takes place. E.g. if the light beam 170 and the light pulse have the same cross section, are co-centric and are parallel, the volume V is essentially the cross-sectional area of the light or pulse multiplied by the distance L.

The first part (atom, molecule, ion, or radical) is present on the first optical path 160 due to the dissociation process. Each dissociation process uses the energy of a photon quantum of the light pulse 710. The energy of a photon of the monochromatic light pulse 710 is $hc/\lambda_{p1}$. Thus, the number of dissociated alkali atoms may be written as:

$$N_M = \xi_M N = \frac{E_{0p1} - E_{p1}}{hc/\lambda_{p1}} \quad (2)$$

wherein $N_M$ is the number of alkali atoms, $E_{0p1}$ is the energy of the light pulse 710 entering the space 110 (or the energy of the second part of the light pulse 710, if the third optical element 744 is used), and $E_{p1}$ is the energy of the attenuated light pulse 715 leaving the space 110. It is assumed, that the decrement of the energy pulse $E_{p0}-E_p$ is totally used to dissociate the gas molecules. By applying the Beer-Lambert law for the light pulse 710:

$$E_{p1} = E_{0p1} \exp\left(-\xi_G \frac{N}{V} \sigma_G L\right) \quad (3)$$

wherein $\xi_G$ is the gas compound content of interest (as measured in proportion, e.g. in ppm or ppb) and $\sigma_G$ is the absorption cross section for the gas compound and the light pulse having wavelength $\lambda_{p1}$. For example, for NaOH at the temperature 300 K the absorption cross $\sigma_G$ for the wavelength 310 nm may be about $(1\text{-}10)\times10^{-18}$ cm$^2$. However, the temperature affects the absorption cross section, and therefore this vale might not be applicable to all measurement cases. The absorption cross sections $\sigma_G$ and $\sigma_M$ are not heavily dependent on temperature, at least for a temperature below 2000° C. On the other hand, the gas compound should be in gaseous form for the applicability of the method. The method is preferably used for gas mixture originating from a thermal process. Thus, the method may be applicable e.g. for a gas mixture having a temperature up to 2000° C., and the method is preferably used for a gas mixture having a temperature in the range from 300° C. to 2000° C. In a higher temperature the dependence of the parameters on temperature should be taken into account.

By using Eqns. (2) and (3), the number of dissociated gas molecules can be calculated. Eq. (3) describes, how much of the energy of the light pulse is used to dissociate the gas molecules, and Eq. (2) describes how this energy is related to the number of dissociated molecules. The number of dissociation induced first parts may be relatively low. The number depends e.g. on the energy of the light pulse and also on the content of gas molecules. As an example 1/10000-1/1000 of the gas molecules 510 may be dissociated with the light pulse 710.

The ratio between the number of molecules or atoms and the volume may be written in terms of other constants using the ideal gas law: pV=NkT, wherein p is the pressure, T is the temperature and k is the gas constant.

Using these equations, one may derive an equation for the gas content:

$$\xi_G = -\ln\left[1 + \ln\left(1 - \frac{I_{k0} - I_k}{I_{k0}}\right) \frac{hc/\lambda_{p1}}{E_{0p1}} \frac{A_p}{\sigma_M}\right] \frac{kT}{p} \frac{1}{\sigma_G L} \quad (4)$$

wherein $A_p$ is the cross sectional area of the light pulse 710. As discussed above, when the intensity profile is non-uniform, an effective area $A_{p,eff}$ may be used instead of $A_p$. Thus, for a coherent light pulse, $A_pL$ is the volume V, wherein the gas molecules are dissociated. An example of the distance L, wherein absorption of light having the wavelength $\lambda_b$ to the first part components takes place, is depicted in FIG. 5*c*. In case the first optical path 160 and the second optical path 800 are not parallel (FIGS. 5*a* and 5*b*), the distance L may be much shorter. In case the paths 160 and 800 are perpendicular, the distance L is of the order if the diameter of the optical pulse, i.e. $2r_2$. For the calculation of the gas content, the optical paths are preferably essentially parallel and essentially co-centric.

Equation 4 assumes e.g. that the light pulse 710 is attenuated only due to absorption to the gas compound 510. In practice, some other absorption or scattering may also take place. However, an equation taking these processes into account is derivable.

From Eq. (4) one may see that the sensitivity of the method depends e.g. on the energy of the light pulse $E_{0p1}$, the area of the light pulse $A_p$, and the distance L. Increasing the pulse energy, increasing the distance L or decreasing the pulse area increases the sensitivity. In principle there is no limit for the distance L. However, in some embodiments, the distance L may range from 1 cm to 50 m.

In the above equations (2) and (3), it was assumed that all the photons of the light pulse 710 that are absorbed in the space 110 dissociate a gas molecule. In a thermal process, scattering and absorption to other molecules may also occur. The accuracy of the method may be improved by measuring the pulse energy $E_{0p1}$ before dissociation with the third photodetector 722 and the pulse energy $E_p$ after dissociation with the second photodetector 720. The difference between these energies may then be compared with the theoretical estimate of Eq. (3). In case deviations from Eq. (3) are large, both energies may be used to deduce a value for the content $\xi_G$.

In the equations 1 to 4 it is assumed the spectral width of the wavelengths of the light beam and light pulse is narrow, i.e. that a monochromatic light beam and a monochromatic light pulse is used.

The pulse energy, $E_{0p1}$, may have a value from 1 nJ to 10 J, preferably from 0.5 μJ to 500 μJ, and in some embodiments, pulse energies of 0.8 μJ, 1.6 μJ, 10 μJ, and 20 μJ have been used. A higher pulse energy may be used to detect lower gas contents. In these embodiments a distance of L=60 cm was used. In other embodiments distances of L=1 m, L=5 m, and L=7 m have been used. Moreover, a coherent and monochromatic light beam 170 having a circular cross section and the diameter of 3 mm was used. It is noted, that the intensities are relatively high. E.g. a 10 μJ pulse having the duration of 10 ns means a power of 1 kW. If the pulse has a circular cross section with the radius of 1 cm, the intensity of the light pulse 710 is approximately 3 MW/m$^2$, i.e. 300 W/cm$^2$.

Measurement Principle, Two-Step Dissociation

It has also been noticed that not all gas molecules can be dissociated with a light pulse to the first part and the second part such that the first part (or the second part) has at least one clear peak in its absorption cross section such that a light beam source for that wavelength would be available. For example, some metal dihalides of the type $M^2H^a{}_2$, wherein metal $M^2$ is a metal (e.g. a heavy metal or an alkaline earth metal from the group II) atom and $H^a$ is a halogen atom (as defined above) are hard to be dissociate to a metal atom and to a dihalide molecule using one photon. For example, lead dichloride, $PbCl_2$ is of this type. Lead dichloride could be dissociated to a lead atom and other compound or compounds using a light pulse having a very short wavelength. For example, for lead chloride, the wavelength might be in the range from 150 nm to 200 nm. However, light sources emitting such high energy pulses are relatively expensive. Moreover, the light having such a short wavelength becomes absorbed to other gases, such as oxygen, and thus cannot propagate long distances. In many application a relatively long measuring distance (i.e. long optical path) is preferable. It was noticed that $PbCl_2$ can be dissociated to a lead (mono)chloride molecule and a chlorine atom. However, the lead (mono)chloride molecule does not have well defines absorption peaks in the visible or near ultraviolet (UV) wavelength. It has absorption bands at the UV regime However, these bands easily mix with absorption bands of other compounds, e.g. $HgCl_2$. Moreover, the absorption cross section at these bands is much smaller than the absorption cross section of lead atom at another wavelength. The ratio of these cross sections may be e.g. in the range $10^{-6}$ to $10^{-5}$. Therefore, the absorption of the gas mixture corresponding to the wavelength(s) of the light beam 170 cannot be significantly increased by dissociation $PbCl_2$ to PbCl and Cl.

Figure 6A:
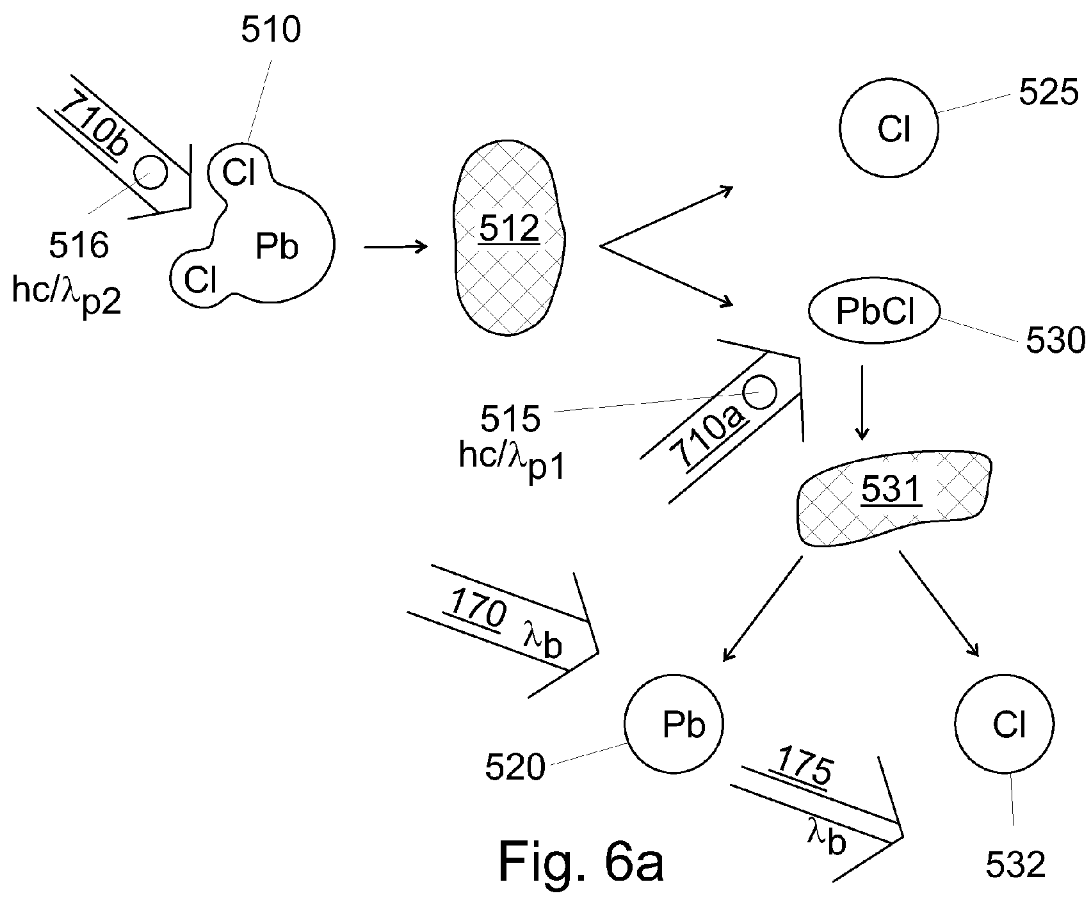
FIG. 6*a* shows the dissociation of a lead chloride molecule to a lead atom and to two chlorine atoms using two optical pulses.

Referring to FIG. 6*a* it was noticed that lead dichloride can be dissociated to a lead atom (i.e. to an excited lead atom) and two chlorine atoms. However, the dissociation is performed in two steps. In the first step, $PbCl_2$ is dissociated to PbCl and Cl. In the second step, PbCl is further dissociated to Pb and Cl. In an embodiment, two subsequent dissociative light pulses of different wavelengths are used. In another embodiment, a single pulse capable of performing both the steps is used. In the latter case, the light pulse may comprise photons arranged to dissociate the molecules in the first step, and further comprise photons arranged to dissociate the molecules in the second step. Moreover, the photons for the first and second step may have the same wavelength. However, the photons for the first and second step may have different wavelength. For example, a light pulse comprising photons having the wavelength 266 nm may dissociate $PbCl_2$ to PbCl and Cl, and further dissociate PbCl to Pb and Cl.

However, it is preferred to dissociate the gas compound molecule in two controlled steps. This may be done using a first light pulse for the first dissociation (e.g. $PbCl_2$ to PbCl and Cl) and a second light pulse for the second dissociation (e.g. PbCl to Pb and Cl). In this case, the photons for the first and second step preferably have different wavelengths. In this way the process is more controlled resulting in easier calibration. Moreover, the calculation of the content of the gas compound becomes simpler.

After the first and second dissociation, the dissociated lead atom is in an excited state. The lifetime of the excited state is very short, only a few nanoseconds. Thus, the measurements should be accurately timed. In particular, if the lifetime of the states into which the second last light pulse 710*b* dissociates the gas molecule 510 is short, timing of the last light pulse 710*a* must be carefully done.

In FIG. 6*a*, the lead dichloride molecule is first dissociated with a second last light pulse 710*b*. The second last light pulse 710*b* comprises photons 516 having the wavelength $\lambda_{p2}$. The second last light pulse 710*b* may further comprise photons having different wavelengths. Preferably the second last light pulse is monochromatic. The wavelength $\lambda_{p2}$ is selected such that the gas molecule 510 (lead dichloride in FIG. 6*a*) is first excited to a molecule 512 in an dissociative state that is further dissociated to the second part 525 (chlorine in FIG. 6*a*) and a third part 530 (lead monochloride in FIG. 6*a*). For lead dichloride, the wavelength $\lambda_{p2}$=355 nm can be used. Here the wavelength is given with the accuracy of one nm.

Thereafter, the third part 530 is excited to a dissociative state 531 with a last light pulse 710*a*. The last light 710*a* pulse comprises the photons 515 having the wavelength $\lambda_{p1}$. The last light pulse 710*a* may further comprise photons having different wavelengths. Preferably the last light pulse is monochromatic. The wavelength $\lambda_{p1}$ is selected such that the third part 530 is excited to a dissociative state 531 with the last light pulse 710*a*. In FIG. 6*a*, where lead monochloride is excited, the wavelength $\lambda_{p1}$=266 nm was used. Thereafter, the dissociative state 531 dissociates to a fourth part 532 (chlorine atom) and to the first part 520 (excited lead atom). The first part 520 is detected using absorption spectroscopy and a light beam 170, as discussed above. The light beam 170 is further attenuated to the attenuated light beam 175 due to absorption to the first part 520; excited lead atom in FIG. 6*a*.

In the embodiment of FIG. 6*a*, the fourth part may be in an exited or in a relaxed state. This does not affect the measurements a lot. However, the first part is in an excited state. As the first part is detected using absorption spectroscopy, the beam wavelength $\lambda_b$ should be selected so that the beam wavelength corresponds to the absorption profile of the excited lead atom. The light beam comprises photons having the beam wavelength $\lambda_b$. The light beam 170 may further comprise photons having different wavelengths. Preferably the light beam 170 is monochromatic. In the embodiment of FIG. 6*a*, a monochromatic light beam with the beam wavelength $\lambda_b$=406 nm was used.

Moreover, as discussed in connection with the one-step dissociation (FIG. 2*b*), also in this case the gas molecule 510 can be excited to an excited state 510*b* before further exciting it to the dissociative state 512. This further, the third (dissociated part) 530 can be excited to a (further) excited state 530*b* (not shown) before further exciting it to the dissociative state 531. Thus, the gas compound molecule 510 may be excited to the dissociative state 512 using at least one photon. Moreover, referring again to FIG. 2*b*, the third part 530 may be excited to the dissociative state 531 using at least one photon. Thus, two photon excitation or multiple photon excitation may be used to excite the molecule 510 or the third part 530.

Figure 6B:
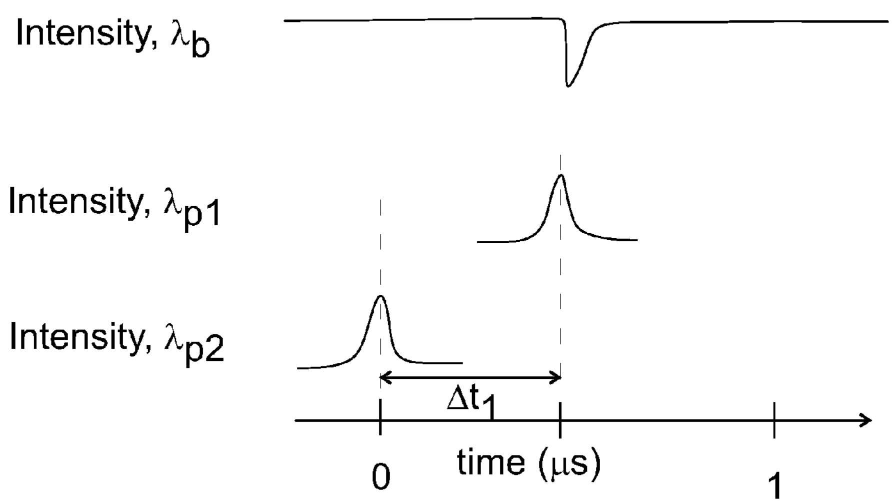
FIG. 6*b* shows the intensity of an attenuated light beam having the wavelength $\lambda_b$ and the intensities of the two light pulses having the wavelengths $\lambda_{p1}$ and $\lambda_{p2}$.

FIG. 6*b* shows the time scales for the measurements of lead dichloride, and the intensities of the light pulses and beam. At time t=0 μs, the second last light pulse 710*b* having the wavelength $\lambda_{p2}$ is emitted. After a time $\Delta t_1$, the last light pulse 710*a* having the wavelength $\lambda_{p1}$ is emitted. These pulses are shown in FIG. 6*b* as the intensity peaks for the corresponding wavelengths. For the light beam 170 the intensity of the attenuated light beam 175 is shown. The intensity of the attenuated light 175 beam having the wavelength $\lambda_b$ decreases soon after the last light pulse 170*a*, because some excited lead atoms are present on the first optical path 160.

The lifetime of the excited state of the lead atom is very short. Therefore, the intensity of the attenuated light beam increases rapidly after the last light pulse. Therefore, in this embodiment, the recovery period is to a large extent defined by the length of the last light pulse 710*a*. Excited lead atoms are present on the first optical path when the last light pulse dissociates the lead chlorine molecules, and only a few nanoseconds after the pulse.

For some other gases the second last light pulse 710*b* may excite the gas atom 510 to the second part 525 and a third part 530, wherein the third part is in an excited state. The wavelength of the last pulse 710*a* may be selected so as to excite the third part 530 from the excited state to the dissociative state 531. Moreover, if the lifetime of the excited state of the third part 530 is short, the last pulse 710*a* has to be timed so that the last pulse 710*a* actually excites the excited third part molecules or radicals. Still further, if the third part 530 is in an excited state, it is possible to time the last pulse such that the third part 530 has enough time to relax from the excited state to a relaxed state or to another excited state before the third part 530 is dissociated. The time for this relaxation may typically be from 1 ns to 100 ns. In this case the wavelength of the last light pulse should be selected such that the last light pulse is capable of dissociating the third part 530 in the relaxed state or the other excited state.

Gas compounds that can be measured using a two-step dissociation include metal halides of the form $M^2H^a{}_2$, wherein $M^2$ is a metal atom such as a Ni or heavy metal atom, e.g. Sn, Cu, Zn, Pb or Hg or an earth alkali metal atom from the group II, and the halogen $H^a$ can be selected from the group of F, CI, Br, I, and At. For example the content of the dichlorides $NiCl_2$, $SnCl_2$, $CuCl_2$, $ZnCl_2$, and $PbCl_2$ are of interest in many thermal processes. Furthermore, some trihalides may be dissociated first to a monohalide. For example, some trihalides of Bi, Sb, and P may be dissociated to a corresponding monohalide using one pulse. The monohalide may be further dissociated to a halogen atom and another atom. These are to be regarded only as example gases for of the method.

As discussed above for the single step dissociation, a single beam may be used to measure two different gas compounds comprising the same atom. E.g. if the gas mixture comprises both lead chloride ($PbCl_2$) and lead bromide ($PbBr_2$), one common light beam may be used to detect both the chloride and the bromide. The lead chloride molecule would be dissociated to lead atom using two light pulses (the last and the second last). Moreover, the lead bromide would be dissociated to lead atom using (i) one other light pulse, (ii) two other pulses, or (iii) one other pulse and one of the last pulse and the second last pulse. Thus, the decrement of the intensity of attenuated light beam after dissociating the lead chloride could be used to determine the lead chloride content. Moreover, the decrement of the intensity of attenuated light beam after dissociating the lead bromide could be used to determine the lead bromide content.

As discussed above for the single step dissociation, two beams or one beam comprising photons corresponding to peak wavelengths of two compounds, may be used to measure two different gas compounds comprising different atoms. E.g. if the gas mixture comprises both lead chloride ($PbCl_2$) and zinc chloride ($ZnCl_2$), two light beams or one light beam comprising photons corresponding to peak wavelengths of zinc and photons corresponding to peak wavelengths of lead, may be used to detect both the chlorides. Possibly the same light pulse source or sources may be used to dissociate both the chlorides. The decrement of the intensity of the attenuated light beam corresponding to the absorption peak of zinc could be used the determine the zinc chloride content. The decrement of the intensity of the attenuated light beam corresponding to the absorption peak of lead could be used the determine the lead chloride content. Thus, a single beam having peaks corresponding to two different atoms may be used to measure the content of two gas compounds. In a similar manner two beams may be used to measure two gas compounds.

Measuring Device, Two-Step Dissociation

Figure 6C:
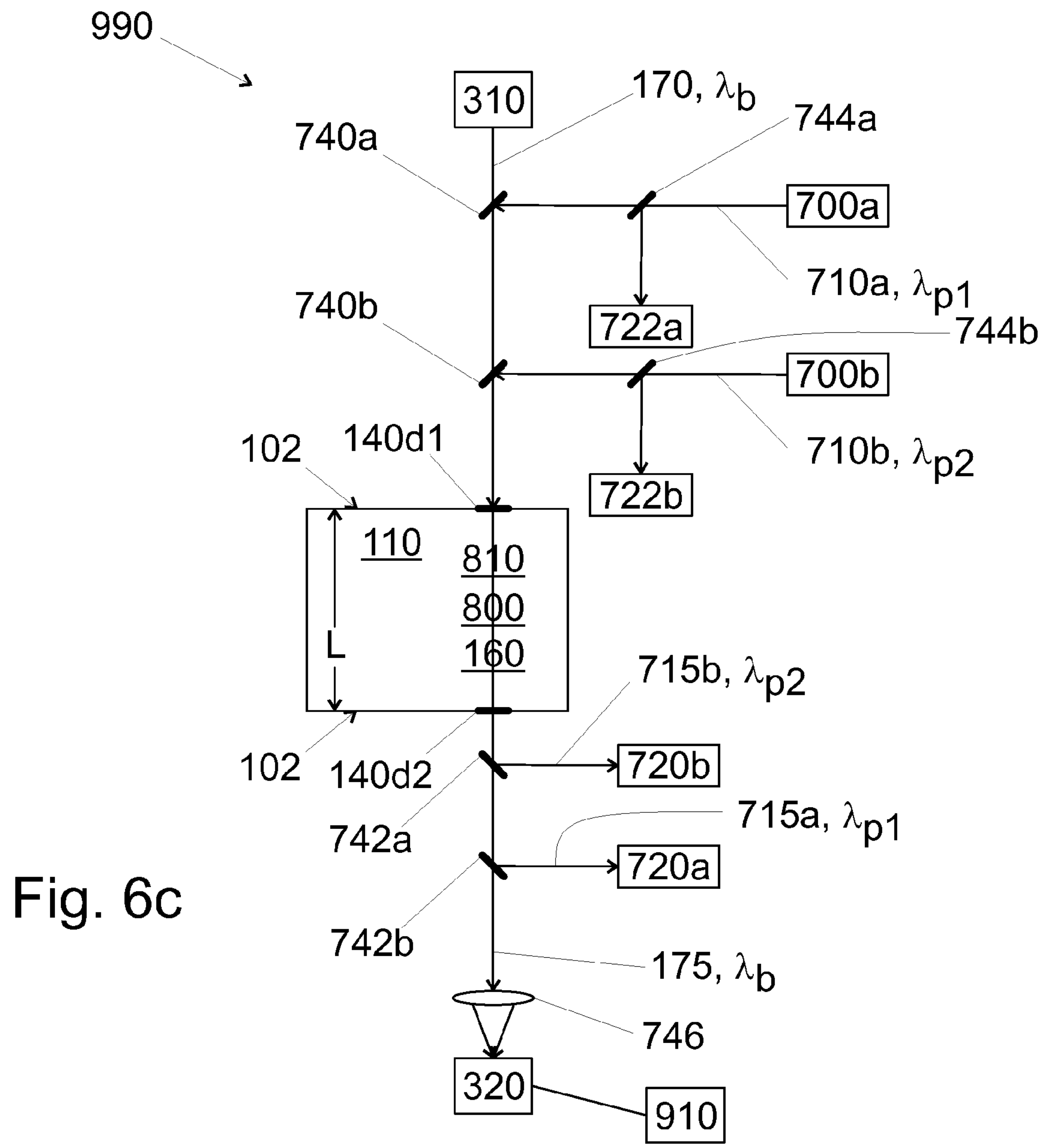
FIG. 6*c* shows a device for measuring the content of a gaseous compound in a gas mixture, capable of emitting two dissociative optical pulses, possibly at two wavelengths.

FIG. 6*c* shows an embodiment of a device 990 for measuring the content of a gas compound 510 from a gas mixture. The device 990 is arranged to use the second last light pulse 710*b* and the last light pulse 710*a* to dissociate the gas molecule to the first part and to the other parts. The device 990 is arranged to use a light beam 170 to detect the content of the first part.

FIG. 6*c* shows a preferred embodiment of the invention using two light pulses to dissociate a gas molecule. The device 990 of FIG. 6*c* comprises:

- a light beam source 310, arranged to emit a monochromatic and coherent light beam 170 having the beam wavelength $\lambda_b$,
- a first light pulse source 700*a*, arranged to emit a monochromatic and coherent last light pulse 710*a* having the pulse wavelength $\lambda_{p1}$,
- optionally, a second light pulse source 700*b*, arranged to emit a monochromatic and coherent second last light pulse 710*b* having the pulse wavelength $\lambda_{p2}$,
- a first optical element 740*a*, arranged to guide
  - the light beam 170 to a first optical path 160 and
  - the last light pulse 710*a* to a second optical path 800 such that the second optical path 800 overlaps the first optical path 160,
- a second optical element 740*b*, arranged to guide
  - the light beam 170 to the first optical path 160,
  - the last light pulse 710*a* to the second optical path 800, and
  - the second last light pulse 710*b* to a third optical path 810 such that the third optical path 810 overlaps the second optical path 800 and the first optical path 160,
- a third optical element 742*a*, arranged to pass the attenuated light beam 175, i.e. light having the wavelength $\lambda_b$, arranged to pass the (attenuated) last light pulse 715*a*, i.e. light having the wavelength $\lambda_{p1}$, and to deflect, reflect, or absorb the attenuated second last light pulse 715*b*, i.e. light having the wavelength $\lambda_{p2}$,
- a fourth optical element 742*b*, arranged to pass the attenuated light beam 175, i.e. light having the wavelength $\lambda_b$, and to deflect, reflect, or absorb the attenuated last light pulse 715*a*, i.e. light having the wavelength $\lambda_{p1}$,

- a fifth optical element 744*a*, arranged to reflect a first part of light having the wavelength $\lambda_{p1}$ and to pass a second part of light having the wavelength $\lambda_{p1}$,
- a sixth optical element 744*b*, arranged to reflect a first part of light having the wavelength $\lambda_{p2}$ and to pass a second part of light having the wavelength $\lambda_{p2}$,
- a first photodetector 320, arranged to detect the intensity of the attenuated light beam 175 having the wavelength $\lambda_b$,
- a lens 746, arranged to converge the attenuated light beam 175 to the first photodetector 320,
- a second photodetector 720*a*, arranged to detect the intensity of attenuated last light pulse 715*a*, the attenuated last light pulse having the wavelength $\lambda_{p1}$,
- a third photodetector 720*b*, arranged to detect the intensity of attenuated second last light pulse 715*b*, the attenuated second last light pulse having the wavelength $\lambda_{p2}$,
- a fourth photodetector 722*a*, arranged to detect the intensity of light having the wavelength $\lambda_{p1}$,
- a fifth photodetector 722*a*, arranged to detect the intensity of light having the wavelength $\lambda_{p2}$, and
- a data processing unit 910, wherein the data processing unit is arranged to calculate the gas compound content in the gas mixture using a first value, the first value being indicative of a first intensity $I_{k0}$ of the attenuated light beam 175 on the photodetector 320, and a second value, the second value being indicative of a second intensity $I_k$ of the attenuated light beam 175 on the photodetector 320.

The second light pulse source is optional. The second light pulse may be negated with the first light pulse source. For example the first light pulse source may emit two subsequent pulses. As another example, the first light pulse source may emit a light pulse that is divided to two pulses. The first of these pulses may be used directly to dissociate the gas molecule 510 or the excited gas molecule, and the last of these pulses may be delayed and used to dissociate the third part 530 (FIG. 6*a*) or the excited third part. Both the first light pulse source, and the light pulse divider may be referred to as means for generating a second light pulse. The second light pulse comprises photons 516 having a second pulse wavelength $\lambda_{p2}$, at least part of the photons 516 dissociating at least part of (i) the gas compound molecules 510 or (ii) excited gas compound molecules 510 on the first optical path 160 third part 530 atoms, molecules, ions, or radicals and to another part 525.

As discussed above, the second pulse source 700*b* may be omitted in some embodiments, wherein a single light pulse is capable of dissociating the third part 530 and the gas molecule 510 (FIG. 6*a*).

As will be seen, the energies of the pulses before dissociations need to be known in order to apply the equation 12 for the gas content. These energies are preferably measured with the photodetectors 722*a* and 722*b*. In case the energies of the light pulses are known without measuring them, the photodetectors 722*a* and 722*b* are optional. Thus the optical components 744*a* and 744*b* are optional. The energies of the light pulses may be known e.g. from calibration measurements, provided that the light pulse sources are stable.

However, the energy of the attenuated light pulses is not necessary needed. Therefore, the photodetector 720*a* is optional. Thus the optical component 742*a* is optional. Therefore also the photodetector 720*b* is optional. Thus the optical components 742*b* is optional.

Preferably light pulses are not guided to the photodetector 320. This may be taken into account by the optical element 742*a*, which may be arranged to pass only photons having approximately the beam wavelength $\lambda_b$ and arranged to reflect or absorb photons 516, 515 of the light pulses 710*b*, 710*a*.

The sizes of the light pulses is preferably selected such that second last light pulse 710*b* has a greater cross section than the last light pulse 710*a*. Moreover, the third optical path 810 (of the second last light pulse 710*b*) and the second optical path 800 (of the last light pulse 710*a*) are preferably essentially parallel and co-centric in the meaning defined for the case of the first and second optical path (cf. above). Therefore, the volume of the second optical path 800 is preferably comprised in volume of the third optical path 810. I.e. the third optical path is greater in diameter than the second optical path.

Furthermore, the size of the last light pulse 710*a* and the light beam 170 is preferably selected such that last light pulse 710*a* has greater cross section than the light beam 170, as discussed for the case of only one dissociative pulse. Moreover, the second optical path 800 (of the last light pulse) and the first optical path 160 (of the light beam) are preferably essentially parallel and co-centric (in the meaning discussed above). Therefore, the volume of the first optical path 160 is preferably comprised in volume of the second optical path 800. I.e. the second optical path is greater in diameter than the first optical path.

In the measurements, the intensity of the attenuated light beam having the wavelength $\lambda_b$ decreases soon after the last light pulse, because some excited lead atoms are present on the first optical path. The attenuated intensity, shown in FIG. 6*b* (top) shows a similar behavior to that depicted already in FIG. 4*c* for the case of a single light pulse.

Wavelength for the light beam 170 may be selected as discussed above for the single pulse dissociation.

Wavelength for the last light pulse 710*a* may be selected as the wavelength for the only light pulse 710, as discussed above for the single pulse dissociation. In particular, the wavelength may be selected such that the third part 530 is dissociated. However, to control the different steps of the dissociation process, the wavelength may be selected also such that the gas compound molecule 510 is not dissociated with the last light pulse, or at least a significant part of the gas compound molecules 510 are not dissociated with the last light pulse.

Wavelength for the second last light pulse 710*b* may be selected such that it dissociated the gas molecule 510. Wavelength of the second last light pulse 710*b* may be e.g. less than 430 nm. In particular, the wavelength may be selected such that the gas compound 510 is dissociated. However, to control the different steps of the dissociation process, the wavelength may be selected also such that the third part 530 is not dissociated with the last light pulse, or at least a significant part of the third parts 530 are not dissociated with the last light pulse. The latter criterion is not critical, since the time between pulses, in particular the time between a last pulse and a subsequent second last pulse, may be selected such that third parts 530 are not present on the optical path at the time of the second last pulse.

Two values, $I_{k0}$ and $I_k$, indicative of the intensity of the attenuated light beam 175 are measured, as discussed above. In the present case, the method comprises

- detecting a second value indicative of a second intensity, $I_k$, of the attenuated light beam 175, wherein the attenuated light beam 175 is further attenuated by the first part 520 atoms, molecules, ions, or radicals on the first optical path 160.

In the present case the first part 520 is produced by the dissociation of the third part 530 molecules or radicals.

The values $I_{k0}$ and $I_k$ may be obtained by averaging or curve fitting, if necessary, as discussed above. These values are obtained for each decrement in the intensity of the attenuated light beam 175, i.e. before and after the last light pulse 710*a*. This was discussed in more detail for the case of dissociation in one step. For example, the value $I_{K0}$ may be selected as the intensity value before the decrement, not as a long term average value. The values are used the determine the content of the gas compound in the gas mixture.

Gas Content, Two-Step Dissociation

From the attenuated intensities $I_{k0}$ and $I_k$ the calculation of the content of the gas compound in the gas mixture may be done as follows when light pulses of two wavelengths are used to dissociate the gas molecule. The calculations are to a great extent similar to the deduction of gas content, when only one light pulse is used (cf. above). In the following calculations it is assumed that

- the light beam 170 is essentially monochromatic,
- the last light pulse 710*a* is essentially monochromatic,
- the second last light pulse 710*b* is essentially monochromatic,
- the optical paths 160, 800, 810 are essentially parallel and co-centric,
- the cross sectional area of the second last light pulse 710*b* is greater than the cross sectional area of the last light pulse 710*a*,
- the cross sectional area of the last light pulse 710*a* is greater than the cross sectional area of the light beam 170,
- the gas compound molecule 510 is assumed to be excited to the dissociative state 512 with a single photon 516 (FIG. 6*a*), and
- the third part 530 is assumed to be excited to the dissociative state 531 with a single photon 515 (FIG. 6*a*).

The calculations are carried out for $PbCl_2$. However, based on the discussion, it is evident for a person skilled in the art how to carry out calculations for other gases.

First, when the second last light pulse 710*b* is guided to the second optical path 810, it dissociates some of the gas molecules 510. Therefore, the pulse energy decreases. By applying the Beer-Lambert law for the second last pulse:

$$\frac{E_{p2}}{E_{0p2}} = \exp\left(-\frac{N_{pbCl_2}}{V}\sigma_{PbCl_2}L\right) \quad (5)$$

Here $E_{0p2}$ is the energy of the second last light pulse 710*b* entering the space 110, $E_{p2}$ is the energy of the attenuated second last light pulse 715*b* coming out from the space 110 and having been attenuated because of exciting the molecules 510 to the molecules 512 in the dissociative state (FIGS. 6*a*, 6*c*). $N_{pbCl2}$ is the number of $PbCl_2$ molecules, V is the volume, where the gas molecules are located, $\sigma_{pbCl2}$ is the absorption cross section for $PbCl_2$ and for the wavelength $\lambda_{p2}$ of the second last pulse, and L is the length of the part of the third optical path 810 that attenuates the second last light pulse. The length may be e.g. the width of the space 110. Assuming no energy losses, i.e. all the decrement in the energy of the second last light pulse is due to exciting the $PbCl_2$ molecules, the number of PbCl molecules may be calculated as:

$$N_{PbCl} = \frac{\frac{E_{0p2}-E_{p2}}{E_{0p2}}}{\frac{hc}{\lambda_{p2}}} = \frac{\left(1-\exp\left(-\frac{N_{PbCl_2}}{V}\sigma_{PbCl_2}L\right)\right)E_{0p2}}{\frac{hc}{\lambda_{p2}}} \quad (6)$$

Here h is the Plank constant and c is the speed of light.

After the second last pulse 710*b* at least some these lead (mono)chloride molecules are present on the second optical path 800. The last light pulse 710*a* is guided through the second optical path 800, whereby at least part of these lead (mono)chloride molecules are excited by the last light pulse 710*a*. By applying the Beer-Lambert law for the last pulse:

$$\frac{E_{p1}}{E_{0p1}} = \exp\left(-\frac{N_{pbCl}}{V_{p2}}\sigma_{PbCl}L\right) \quad (7)$$

Here $E_{0p1}$ is the energy of the last light pulse 710*a* entering the space 110, $E_{p1}$ is the energy of the attenuated last light pulse 715*a* coming out from the space 110 and having been attenuated e.g. because of exciting the molecules 530 to the excited state 531 (FIGS. 6*a*, 6*c*). $N_{PbCl}$ is the number of PbCl molecules, $V_{p2}$ is the volume, where the PbCl gas molecules are located (note: $V_{p2}$ is also the volume of the optical path for the second last light pulse, since PbCl is produced by the second last light pulse induced dissociation), $\sigma_{PbCl}$ is the absorption cross section for PbCl and for the wavelength $\lambda_{p1}$ of the last pulse. L is the length of the part of the second optical path 800 that attenuates the last light pulse. The length may be e.g. the width of the space 110. As is evident, in these calculations these lengths are assumed equal. However, in case a device 990 is located in ambient, these length are not necessarily equal. As above, the number of thus excited molecules, which equals the number of lead atoms, since each excited PbCl molecule dissociates, may be calculated as:

$$N_{Pb} = \frac{\frac{E_{0p1}-E_{p1}}{E_{0p1}}}{\frac{hc}{\lambda_{p1}}} = \frac{\left(1-\exp\left(-\frac{N_{PbCl}}{V_{p2}}\sigma_{PbCl}L\right)\right)E_{0p1}}{\frac{hc}{\lambda_{p1}}} \quad (8)$$

The light beam 170 becomes further attenuated by the presence of (excited) lead atoms (or more generally first parts 520) on the first optical path 160. Therefore, the ratio of the attenuated light beam 175 and further attenuated light beam 175 can be written as:

$$\frac{I_k}{I_{k0}} = \exp\left(-\frac{N_{pb}}{V_{p1}}\sigma_{Pb}L\right) \Leftrightarrow N_{pb} = \frac{-\ln\left(\frac{I_k}{I_{k0}}\right)V_{p1}}{\sigma_{Pb}L} \quad (9)$$

Here $V_{p1}$ is the volume of the second optical path, i.e. the volume in which the last light pulse 710*a* dissociates the lead (mono)chloride molecules to excited lead atoms. The attenuation of the light beam 170 is due to the presence of these excited lead atoms. Inserting $N_{Pb}$ from Eq. 9 to Eq. 8 and solving for $N_{PbCl}$ gives:

$$N_{PbCl} = -\ln\left(1 - \frac{N_{Pb}hc}{\lambda_{p1}E_{0p1}}\right)\frac{V_{p2}}{\sigma_{PbCl}L} \tag{10}$$

Inserting $N_{PbCl}$ from Eq. 10 to Eq. 6 may be used to calculate the number of lead (di)chloride molecules $N_{PbCl2}$. However, the content of the gas compound in a gas mixture is often of more interest. From gas theory it is known that:

$$N_{PbCl_2} = \xi_{PbCl_2}N = \xi_{PbCl_2}\frac{pV}{kT} \Leftrightarrow \frac{N_{PbCl_2}}{V} = \xi_{PbCl_2}\frac{p}{kT} \tag{11}$$

Here $\xi_{PbCl2}$ is the content of lead (di)chloride in a gas mixture. Inserting Eqs. 11 and 10 into Eq. 6, gives for the content of the gas compound:

$$\xi_{PbCl_2} = -\ln\left\{1 + \ln\left[1 + \ln\left(\frac{I_k}{I_{k0}}\right)\frac{A_{p1}hc}{\sigma_{Pb}E_{0p1}\lambda_{p1}}\right]\frac{A_{p2}hc}{\sigma_{PbCl}E_{0p2}\lambda_{p2}}\right\}\frac{kT}{p}\frac{1}{\sigma_{PbCl_2}L} \tag{12}$$

Here also the equation $V_{p2}=A_{p2}L$ and $V_{p1}=A_{p1}L$ have been used. From Eq. 12 the lead chloride content may be calculated, once the parameters are known. As discussed above, e.g. in the context of equation 4, effective areas can be used instead of $A_{pt}$ and $A_{p2}$ if the intensity profile is not uniform.

As in equation 4, also equation 12 assumes e.g. that the light pulses 710*a*, 710*b* are attenuated only due to absorption to the gas compound 510 and to the third part 530. In practice, some other absorption or scattering may also take place. However, an equation taking these processes into account is derivable.

Equation 12 assumes e.g. that the second last light pulse 710*b* is attenuated only due to absorption to the gas compound 510, and the last light pulse 710*a* is attenuated only due to absorption to the third part 530.

In practice, some other absorption or scattering may also take place. However, an equation taking these processes into account is derivable.

At the temperature T=1000 K and pressure $p=1.012\times10^5$ Pa and for the wavelengths discussed above, the values of some of the parameters are: $h=6.626\times10^{-34}$ Js, $c=2.998\times10^8$ m/s, $k=1.38\times10^{-23}$ J/K, $\lambda_{p1}=266\times10^{-9}$ m, $\lambda_{p2}=355\times10^{-9}$ m, $\lambda_b=406\times10^{-9}$ m, $\sigma_{PbCl2}=10^{-21}$ m$^2$, and $\sigma_{Pb}=10^{-16}$ m$^2$.

The other constants depend on pulse energy, pulse size, and length of the optical path. For example, these may be $E_{0p2}=50\times10^{-3}$ J, $E_{0p1}=50\times10^{-6}$ J, $A_{p1}=25\times10^{-6}$ m$^2$, $A_{p2}=25\times10^{-6}$ m$^2$, and L=1 m. It is further noted, that if the detection limit for $I_k/I_{k0}$ is e.g. 0.01, the detection limit for the gas (lead chloride) content is about 0.7 ppm.

Measurement Principle, Three-Step Dissociation

Figure 7A:
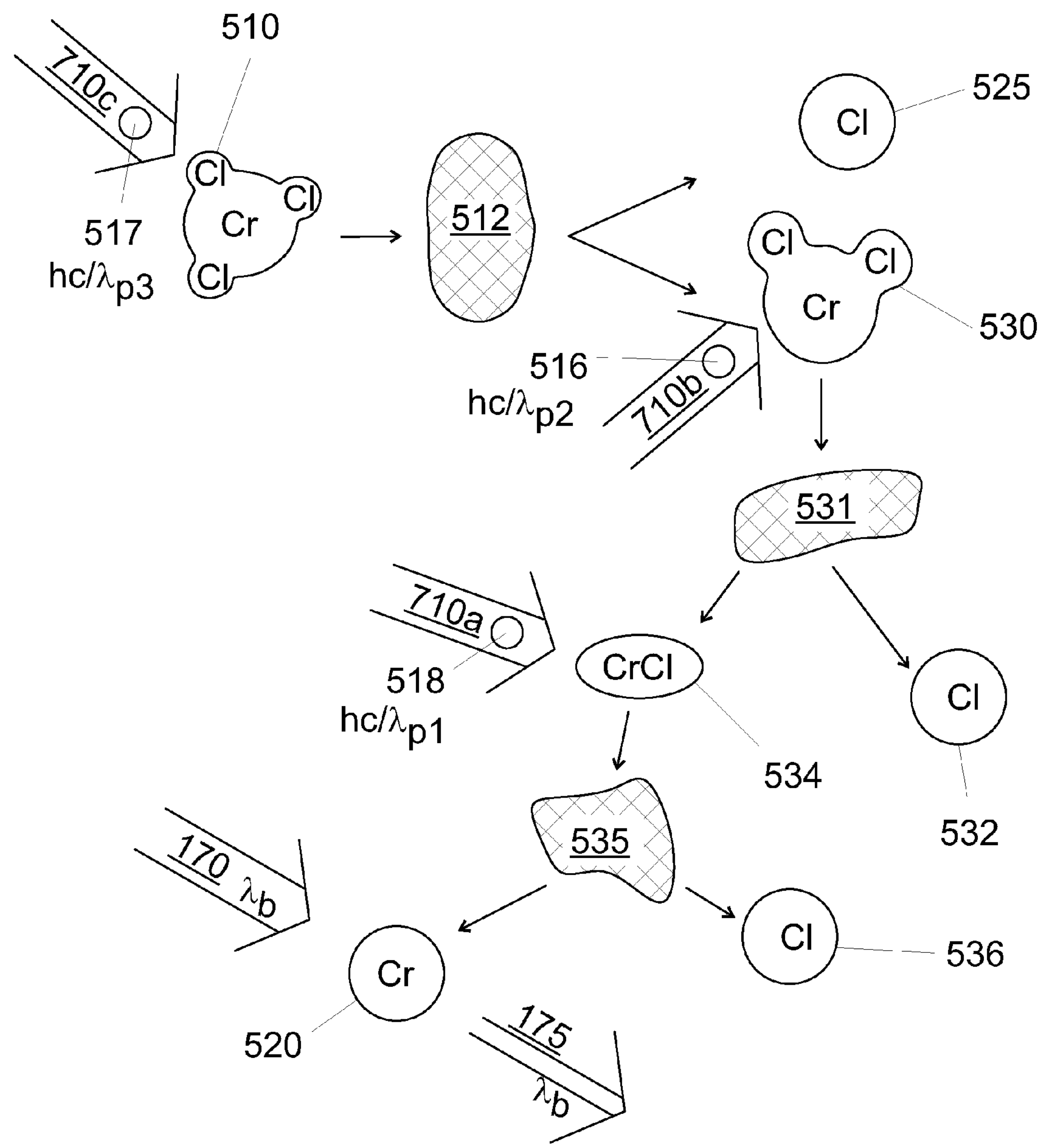
FIG. 7*a* shows the dissociation of a chromium chloride molecule to a chromium atom and to three chlorine atoms using three optical pulses.

It has further been noticed that the content of some gas compound molecules 510 in a gas mixture may be measured using three subsequent light pulses to dissociate the gas molecule. Referring to FIG. 7*a*, a chromium chloride $CrCl_3$ molecule 510 may dissociated using three subsequent dissociative light pulses to an chromium atom (first part 520), which may or may not be in an excited state, and to other parts (530, 532, 536), wherein the other parts are chlorine atoms.

The chromium (tri)chloride molecule 510 (gas molecule) may be excited with a third last light pulse 710*c* to the gas molecule 512 in a dissociative state. The third last light pulse 710*c* comprises photons 517 having the third pulse wavelength $\lambda_{p3}$. The third last light pulse 710*c* may further comprise photons having another wavelength. Preferably the third last light pulse 710*c* is monochromatic. The third pulse wavelength $\lambda_{p3}$ is selected so as to excite the gas molecule 510 to the excited gas molecule 512 in a dissociative state. The gas molecule 512 dissociates to the second part 525 and to the third part 530. In FIG. 7*a* the second part 525 is a chlorine atom and the third part 530 is an chromium (di) chloride molecule.

The chromium (di)chloride molecule 530 (third part) may be excited with a second last light pulse 710*b* to an excited third part 531 in a dissociative state. The second last light pulse 710*b* comprises photons 516 having the second pulse wavelength $\lambda_{p2}$. The second last light pulse 710*b* may further comprise photons having another wavelength. Preferably the second last light pulse 710*b* is monochromatic. The second pulse wavelength $\lambda_{p2}$ is selected so as to excite the third part 530 to an excited third part 531 in a dissociative state. The excited third part 531 dissociates to a fourth part 532 and to a fifth part 534. In FIG. 7*a* the fourth part 532 is a chlorine atom and the fifth part 534 is an chromium (mono)chloride molecule.

The chromium (mono)chloride molecule 534 (fifth part) may be excited with the last light pulse 710*a* to an excited fifth part 535 in a dissociative state. The last light pulse 710*a* comprises photons 515 having the first pulse wavelength $\lambda_{p1}$. The last light pulse 710*a* may further comprise photons having another wavelength. Preferably the last light pulse 710*a* is monochromatic. The first pulse wavelength is selected so as to excite the fifth part 534 to an excited fifth part 535 in a dissociative state. The excited fifth part 535 dissociates to the first part 520 and to a sixth part 536. In FIG. 7*a* the first part 520 is a chromium atom and the sixth part 536 is a chlorine atom.

The first part 520 (i.e. the chromium atom) may be in a relaxed state or in an excited state. Also the other parts 525, 530, 532, 534, and 536 may be in a relaxed state or in an excited state. The wavelength of the second last light pulse 710*b* is selected so that the third part 530 is excited to a dissociable state, taking into account whether the third part 530 is in an excited state or in a relaxed state. The wavelength of the last light pulse 710*a* is selected so that the fifth part 534 is excited to a dissociable state, taking into account whether the fifth part 534 is in an excited state or in a relaxed state.

The first part 520 is probed with the light beam 170, which attenuates to the attenuated light beam 175. The attenuation may be due to at least one of (i) absorption due to first part atoms, molecules, ions, or radicals produced in the dissociation of gas molecules using the last light pulse 710*a*, and (ii) other processes such as scattering or absorption by other compounds or particles, whereby the first value indicative of the intensity of the attenuated light beam may be measured, as discussed above. In addition, the attenuation may be due to (iii) absorption due to other first part atoms, molecules, ions, or radicals produced by other dissociation processes of the gas molecules, e.g. produced by thermal dissociation, whereby the second value indicative of the intensity of the attenuated light beam may be measured, as discussed above.

The light beam 170 comprises photons having the beam wavelength $\lambda_b$. The last light beam 170 may further comprise photons having another wavelength. Preferably the light beam 170 is monochromatic. The beam wavelength $\lambda_b$ is selected so that it corresponds to the absorption profile of the first part 520 (excited or relaxed). Thus, the dissociation of the gas molecule 510 eventually to the first part 520 increases the absorption of the light beam to the gas mixture at the beam wavelength $\lambda_b$.

The third part 530 may be in an excited state, wherein the lifetime of the excited state is short. Therefore, the timing of the second last light pulse 710*b* needs to be selected so as to excite the third part 530 to a dissociative state.

The fifth part 534 may be in an excited state, wherein the lifetime of the excited state is short. Therefore, the timing of the last light pulse 710*a* needs to be selected so as to excite the fifth part 534 to a dissociative state.

Two photon excitation or multiple photon excitation may be used to excite at least one of the gas molecule 510, the third part 530, and the fifth part 534, to the corresponding dissociative state, as discussed above in the context of one step dissociation and two step dissociation. Gases that may be possible to measure with the three step dissociation include also some other metal trichlorides such as $FeCl_3$, $AlCl_3$, and $ThCl_3$.

Measuring Device, Three-Step Dissociation

Figure 7B:
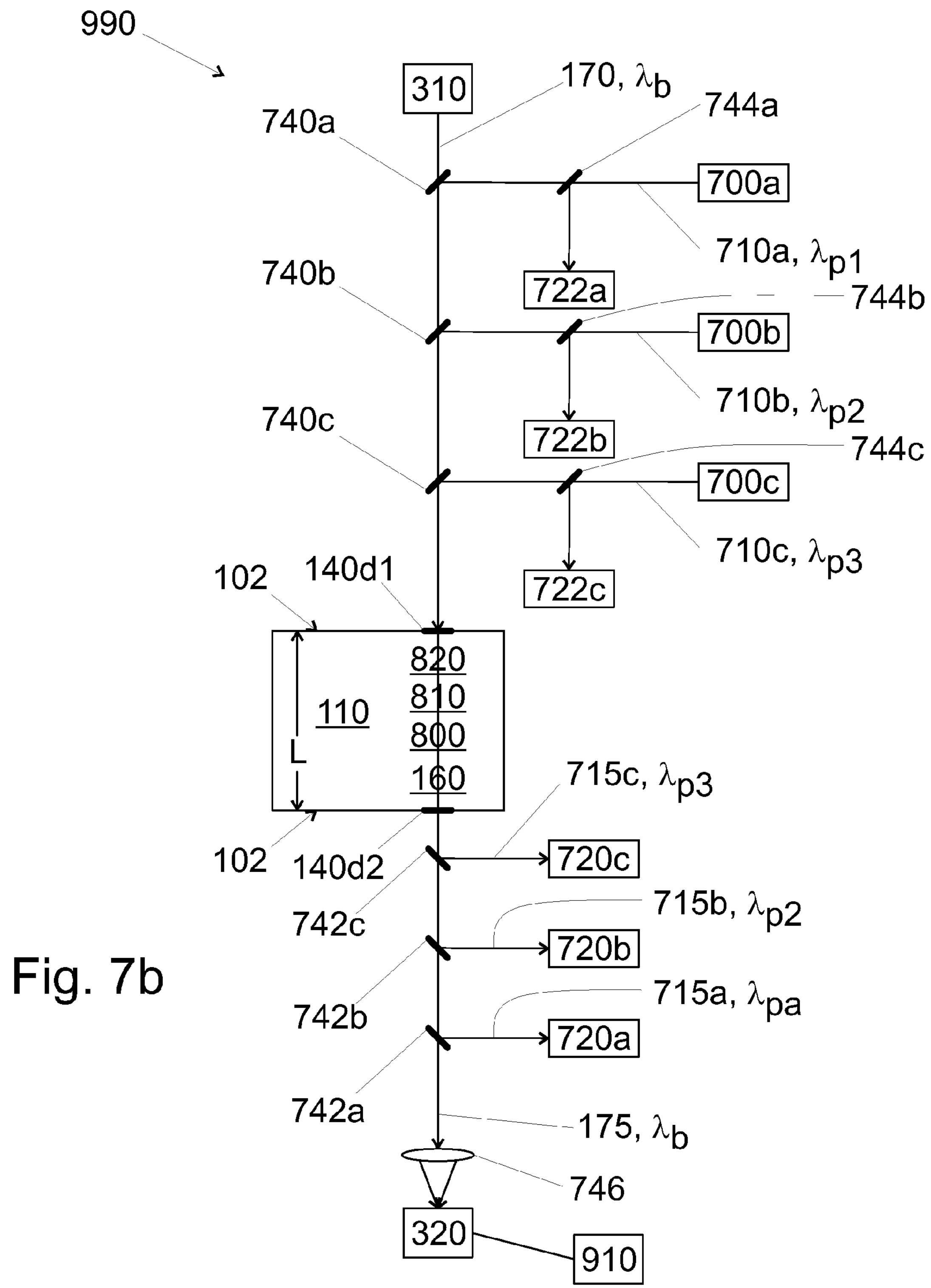
FIG. 7*b* shows a device for the measuring the content of a gaseous compound in a gas mixture, capable of emitting three dissociative optical pulses, possibly at three wavelengths.

FIG. 7*b* shows an embodiment of a device 990 for measuring the content of a gas compound 510 from a gas mixture. The device 990 is arranged to use the third last light pulse 710*c*, the second last light pulse 710*b* and the last light pulse 710*a* to dissociate the gas molecule 510 to the first part 520 and to the other parts (525, 530, 532, 534, 536; FIG. 7*a*). The device 990 is arranged to use the light beam 170 to detect the content of the first part.

In addition to the components shown in FIG. 6*c*, the device of FIG. 7*b* further comprises:

- a third light pulse source 700*c*, arranged to emit a monochromatic and coherent third last light pulse 710*c* having the pulse wavelength $\lambda_{p3}$,
- a seventh optical element 740*c*, arranged to guide
  - the light beam 170 to the first optical path 160,
  - the last light pulse 710*a* to the second optical path 800,
  - the second last light pulse 710*b* to the third optical path, and
  - the third last light pulse 710*c* to a fourth optical path 820 such that the fourth optical path 820 overlaps the third optical path 810, the second optical path 800, and the first optical path 160,
- an eighth optical element 742*c*, arranged to pass the attenuated light beam 175, i.e. light having the wavelength $\lambda_b$, arranged to pass the (attenuated) last light pulse 715*a*, i.e. light having the wavelength $\lambda_{p1}$, arranged to pass the (attenuated) second last light pulse 715*b*, i.e. light having the wavelength $\lambda_{p2}$, and to deflect or reflect the attenuated third last light pulse 715*c*, i.e. light having the wavelength $\lambda_{p3}$,
- a ninth optical element 744*c*, arranged to reflect a first part of light having the wavelength $\lambda_{p3}$ and to pass a second part of light having the wavelength $\lambda_{p3}$,
- a sixth photodetector 720*c*, arranged to detect the intensity of attenuated third last light pulse 715*c*, the attenuated third last light pulse having the wavelength $\lambda_{p3}$,
- a seventh photodetector 722*c*, arranged to detect the intensity of light having the wavelength $\lambda_{p3}$.

As discussed above in connection with the second light pulse source, the third light pulse source 700*c* is optional. More generally the device comprises means for generating a third last light pulse 710*c* having the pulse wavelength $\lambda_{p3}$. The means may comprise at least one of the first light pulse source, the second light pulse source, and a light pulse divider.

As discussed above, the photodetectors 720*c*, 720*b*, and 720*a* are optional. Thus the optical components 742*c*, 742*b*, and 742*a* are optional.

However, preferably light pulses are not guided to the photodetector 320. This may be taken into account by the optical element 742*a*. Moreover, measuring the gas content may require information on the energy of the light pulses. The energy of the pulses may be measured with the photodetectors 722*a*, 722*b*, and 722*c*. In case the energy is otherwise known, the photodetectors 722*a*, 722*b*, and 722*c* are optional, whereby the optical elements 744*a*, 744*b*, and 744*c* are optional. The energy of the attenuated pulses may be measured with the photodetectors 720*a*, 720*b*, and 720*c*.

The optical paths 160, 800, 810, 820 are preferably parallel and co-centric.

The sizes of the light pulses is preferably selected such that third last light pulse 710*c* has a greater cross section then the second last light pulse 710*b*. Moreover, the fourth optical path 820 (of the third last light pulse) and the third optical path 810 (of the second last light pulse) are preferably essentially parallel and co-centric in the meaning discussed above. Therefore, the volume of the third optical path 810 is preferably comprised in volume of the fourth optical path 820. I.e. the fourth optical path is greater in diameter than the third optical path.

Furthermore, the size of the second last light pulse 710*b* is preferably selected such that second last light pulse 710*b* has a greater cross section then the last light pulse 710*a*. Moreover, the third optical path 810 (of the second last light pulse) and the second optical path 800 (of the last light pulse) are preferably essentially parallel and co-centric in the meaning discussed above. Therefore, the volume of the second optical path 800 is preferably comprised in volume of the third optical path 810. I.e. the third optical path is greater in diameter than the second optical path.

Still further, the size of the last light pulse 710*a* and the light beam 170 is preferably selected such that last light pulse 710*a* has greater cross section than the light beam 170. Moreover, the second optical path 800 (of the last light pulse) and the first optical path 160 (of the light beam) are preferably essentially parallel and co-centric in the meaning discussed above. Therefore, the volume of the first optical path 160 is preferably comprised in volume of the second optical path 800. I.e. the second optical path is greater in diameter than the first optical path.

Other Features

The device 990 may comprise an integrated light source. The integrated light source comprises at least two of the light beam source 310, the third light pulse source 700*c*, the second light pulse source 700*b*, the first light pulse source 700*a*, and the light pulse source 700. The integrated light source is may be arranged to emit light such that the optical paths are essentially parallel. At least none of the light beam and the light pulses may be guided using reflectors inside the integrated light source. In addition, at least none of the light beam and the light pulses may be guided using at least one optical fiber inside the integrated light source.

Figure 8:
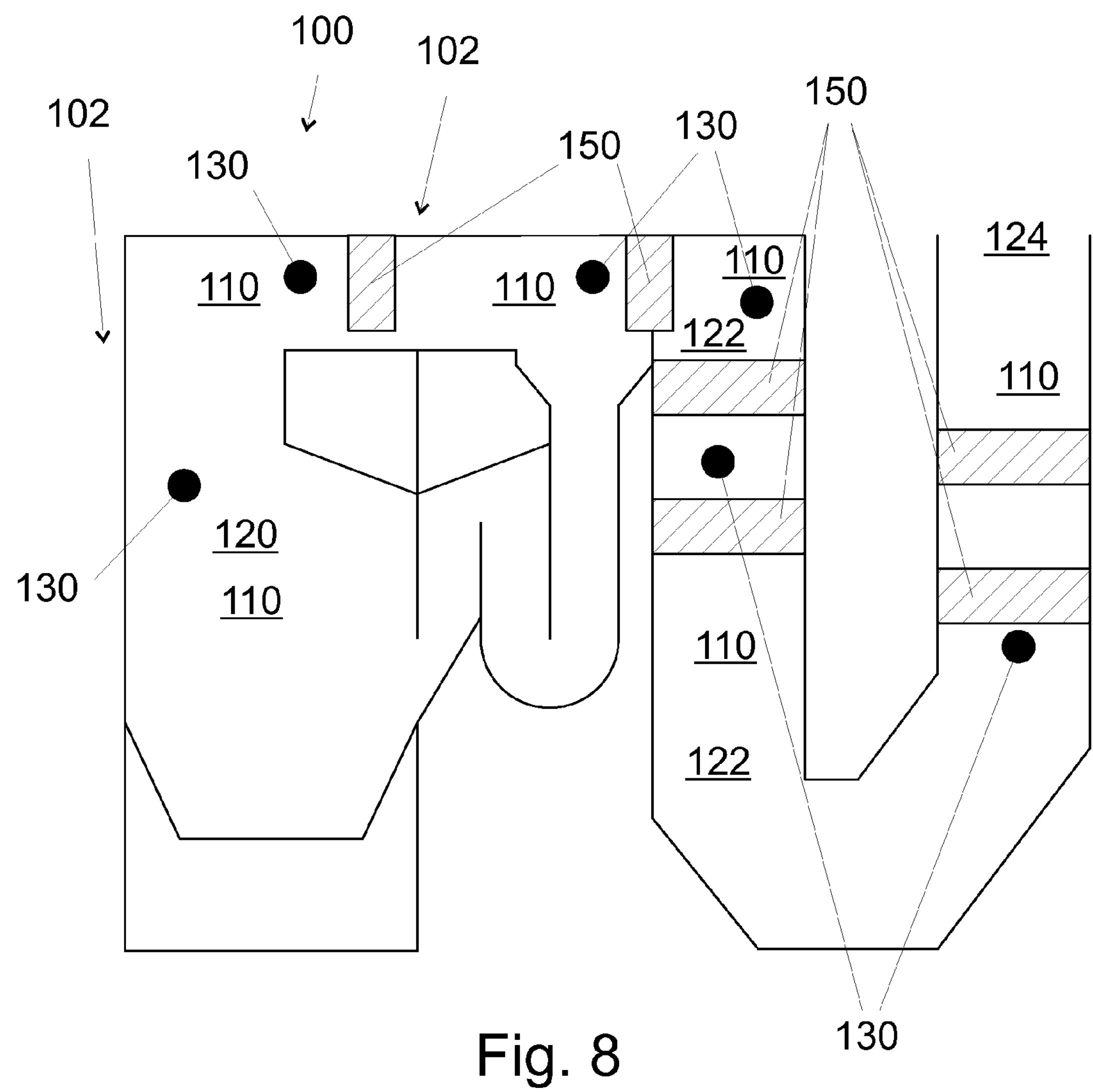
FIG. 8 shows a boiler and possible locations for optical measurements within the boiler.

The device 990 may be integrated with a boiler. Thus the content of a gas compound emitted by the boiler, e.g. in the flue gases, may be measured. The measurement may be made in situ. FIG. 8 shows an embodiment of a boiler 100. The device 990 for measuring the gas content may be integrated with the boiler. The device may be integrated e.g. such that the boiler 100 comprises at least one optical inlet 130. The boiler 100 may comprise at least one optical outlet 135 (cf. FIGS. 1*a*-1*d*).

The boiler 100 of FIG. 8 comprises the walls 102. The walls 102 separate the interior of the boiler and the exterior of the boiler. Therefore, also the ceiling and the floor are considered walls 102. In the interior of the boiler the space 110 is formed. The space 110 may comprise e.g. a combustion space 120, a flue gas channel 122, and/or a chimney 124. The boiler 100 comprises heat exchangers 150 located in the space 110. A heat exchanger 150 may be e.g. a superheater device, an economizer, an air pre-heater, or a feed-water pre-heater. The boiler 100 comprises, in at least one wall 102, at least one optical inlet 130, such as a window 140 or a hole 132, for the optical measurements. A window 140 is transparent so that light can propagate through the window. Preferably the light of the measuring light beam is not significantly attenuated while travelling through the window. The boiler 100 may comprise at least one optical outlet 135, such as a window 140 or a hole 132. In case a hole 132 is used as an optical inlet, air or other gas may be blown through the hole 132 into the boiler 100 in order to retain the flue gases in the boiler 100.

In a similar manner the device 990 may be integrated with a gasification reactor. The gasification reactor is arranged to gasify biomass to synthesis gas.

In a similar manner the device 990 may be integrated with a pyrolysis reactor. The pyrolysis reactor is arranged to thermochemically decompose organic material at elevated temperatures.

In a similar manner the device 990 may be integrated with a torrefaction reactor. The torrefaction reactor is arranged to thermochemically extract volatile components from organic material at elevated temperatures (lower temperatures than in the pyrolysis reactor).

The method is not limited to the described embodiments, but can be used within the scope claims.

The invention claimed is:

1. A method for measuring the content of a gas compound from a gas mixture, wherein the gas compound consists of gas compound molecules, the method comprising generating a light beam, wherein the light beam comprises photons having a beam wavelength, guiding the light beam to a first optical path, wherein the first optical path runs through a space containing the gas mixture comprising the gas compound, whereby the light beam is attenuated to an attenuated light beam, detecting a first value indicative of a first intensity of the attenuated light beam, generating a last light pulse, wherein the last light pulse comprises photons having a first pulse wavelength, and optionally generating another light pulse, wherein the light beam is monochromatic or essentially monochromatic having said beam wavelength, and the last light pulse is monochromatic or essentially monochromatic having said first pulse wavelength, the method further comprising guiding at least part of the last light pulse to a second optical path such that the second optical path is essentially parallel to the first optical path, dissociating at least part of the gas compound molecules or at least part of excited gas compound molecules on the first optical path to at least two dissociated parts using the last light pulse or the another light pulse, dissociating (i) at least part of the gas compound molecules, (ii) at least part of excited gas compound molecules, (iii) at least part of the dissociated parts, or (iv) at least part of the excited dissociated parts on the first optical path to first part atoms, molecules, ions, or radicals, and to another part using the last light pulse, whereby the light beam is further attenuated by absorption to the first part atoms, molecules, ions, or radicals on the first optical path, selecting the beam wavelength such that it corresponds to the absorption profile of the first part, detecting a second value indicative of a second intensity of the further attenuated light beam, and determining, using the first value and the second value, the gas compound content of the gas mixture.

2. The method of claim 1, comprising dissociating at least part of (i) the gas compound molecules or (ii) excited gas compound molecules on the first optical path to first part atoms, molecules, ions, or radicals, and to another part using the last light pulse.

3. The method of claim 1, comprising generating the another light pulse, wherein the another light pulse comprises photons having a second pulse wavelength, dissociating at least part of (i) the gas compound molecules or (ii) excited gas compound molecules on the first optical path to third part atoms, molecules, ions, or radicals, and to another part using the another light pulse, and dissociating at least part of (i) the third part atoms, molecules, ions, or radicals or (ii) the excited third part atoms, molecules, ions, or radicals to the first part atoms, molecules, ions, or radicals, and to another part using the last light pulse.

4. The method of claim 1, comprising dissociating at least part of second gas compound molecules or at least part of excited second gas compound molecules on the first optical path to at least two dissociated parts, generating a second light beam, wherein the second light beam comprises photons having a second beam wavelength, detecting a third value indicative of a first intensity of an attenuated second light beam, detecting a fourth value indicative of a second intensity of the attenuated second light beam, and determining, using the third value and the fourth value, the content of the second gas compound content of the gas mixture.

5. The method of claim 1, comprising optionally detecting a third value indicative of an intensity of the attenuated light beam, generating another light pulse, wherein the another light pulse comprises photons having another pulse wavelength, dissociating at least part of (i) second gas compound molecules or (ii) excited second gas compound molecules on the first optical path using the another light pulse, whereby the light beam is further attenuated by absorption (i) to a dissociation product of the second gas compound molecules or (ii) to a dissociation product of the excited second gas compound molecules on the first optical path, detecting a fourth value indicative of a second intensity of the further attenuated light beam, determining, using the fourth value and at least one of the third value and the first value, the content of the second gas compound content of the gas mixture.

6. The method of claim 1, wherein the last light pulse comprises photons having the first pulse wavelength, wherein the first pulse wavelength is at most 430 nm and at least one of the photons is capable of exciting the gas compound molecule, the excited gas compound molecule, a dissociated part, or an excited dissociated part to a dissociative state having an energy of at least 2.88 eV above the ground state of the gas compound molecule or the ground state of the dissociated part and/or the light beam comprises photons having the beam wavelength, wherein the beam wavelength is at most 1800 nm.

7. The method of claim 1, wherein the light beam has a first cross section, the last light pulse has a second cross section, and the second cross section is greater than the first cross section.

8. The method of claim 1, wherein the first optical path and the second optical path are essentially co-centric.

9. The method of claim 1, comprising producing the gas mixture in a thermal process, wherein the thermal process is one of combustion, pyrolysis, gasification, and torrefaction, wherein the gas mixture comprises the gas compound molecules.

10. A device for measuring the content of a gas compound from a gas mixture, wherein the gas compound consists of gas compound molecules, comprising a light beam source, arranged to emit a light beam comprising photons having a beam wavelength and a photodetector, wherein the light beam source is a laser, a first optical path is arranged optically between the photodetector and the light beam source, a space, through which the first optical path is arranged to run, is arranged to contain the gas mixture absorbing the light beam, the light beam is arranged to be attenuated to an attenuated light beam by said absorption of the light beam, and the photodetector is arranged to detect a first value indicative of a first intensity of the attenuated light beam, the device comprising at least a first light pulse source, wherein the first light pulse source is arranged to generate a last light pulse comprising photons having a first pulse wavelength, at least part of the photons dissociating at least part of (i) gas compound molecules, (ii) excited gas compound molecules, (iii) dissociated parts or (iv) excited dissociated parts on the first optical path to first part atoms, molecules, ions, or radicals, and to another part, wherein the light beam is further attenuated by absorption to first part atoms, molecules, ions, or radicals on the first optical path, wherein the dissociated parts have optionally been produced from the gas compound molecules by dissociation using at least another light pulse, wherein the beam wavelength is selected such that it corresponds to the absorption profile of the first part, the photodetector is arranged to detect a second value indicative of a second intensity of the further attenuated light beam, and the device comprises a first optical element, wherein the first optical element is arranged (i) to guide the light beam to the first optical path and (ii) to guide the last light pulse to a second optical path, wherein (iii) the second optical path is essentially parallel to the first optical path, and a processor arranged to determine, using the first value and the second value, the gas compound content in the gas mixture.

11. The device of claim 10, wherein the first light pulse source is arranged to generate the last light pulse comprising photons having a first pulse wavelength, at least part of the photons dissociating at least part of (i) gas compound molecules or (ii) excited gas compound molecules on the first optical path to the first part atoms, molecules, ions, or radicals, and to another part.

12. The device of claim 10, wherein the device comprises means for generating the another light pulse, wherein the another light pulse comprises photons having a second pulse wavelength, at least part of the photons dissociating at least part of (i) gas compound molecules or (ii) excited gas compound molecules on the first optical path to third part atoms, molecules, ions, or radicals and to another part, and the first light pulse source is arranged to generate the last light pulse comprising photons having a first pulse wavelength, at least part of the photons dissociating at least part of (i) the third part atoms, molecules, ions, or radicals or (ii) excited third part atoms, molecules, ions, or radicals to first part atoms, molecules, ions, or radicals, and to another part.

13. The device of claim 10, wherein the first light pulse source is a laser.

14. The device of claim 10, wherein the first optical path and the second optical path are essentially co-centric.

15. The device of claim 10, wherein the light beam source is arranged to emit a light beam having a first cross section, and the first light pulse source is arranged to emit the last light pulse having a second cross section, such that the second cross section is greater than the first cross section.

* * * * *